US005993826A

United States Patent [19]
Hansen et al.

[11] Patent Number: 5,993,826
[45] Date of Patent: *Nov. 30, 1999

[54] METHODS AND COMPOSITIONS RELATING TO USEFUL ANTIGENS OF *MORAXELLA CATARRHALIS*

[75] Inventors: Eric J. Hansen, Plano, Tex.; Meria E. Helminen, Helsinki, Finland; Isobel Maciver, Dallas, Tex.

[73] Assignee: Board of Regents, The University of Texas, Austin, Tex.

[ * ] Notice: This patent is subject to a terminal disclaimer.

[21] Appl. No.: 08/025,363

[22] Filed: Mar. 2, 1993

Related U.S. Application Data

[63] Continuation-in-part of application No. PCT/US92/06869, Aug. 14, 1992, which is a continuation-in-part of application No. 07/745,591, Aug. 21, 1991, Pat. No. 5,552,146.

[51] Int. Cl.$^6$ ........................ A61K 39/102; A61K 39/02; C07K 14/285; C07K 16/102
[52] U.S. Cl. .................................... 424/251.1; 424/184.1; 530/350; 530/388.1; 530/388.2; 435/69.1; 435/69.3
[58] Field of Search ........................... 424/88, 92, 184.1, 424/251.1; 530/350, 388.1, 388.2; 435/69.1, 71.1, 69.3

[56] References Cited

U.S. PATENT DOCUMENTS 4,271,147  6/1981  Helting et al. ............................ 424/91

FOREIGN PATENT DOCUMENTS

WO 90/12114  6/1990  WIPO .

OTHER PUBLICATIONS

Bartos et al The Journal of Infect Dis 158: 761–765 1988.
Murphy The American Journ of Medicine 88: 41S–45S.
Goldblatt et al The Joun of Infect Dis. 162: 1128–1135, 1990.
Helminen et al. Infect & Immunity 61: 2003–2010 1993.
McGehee Am Journal of Respir. Cell Mol. Biol. 1: 201–216, 1989.
Doyle et al Peditr Infect Dis J. 8: 545–547 1989.
(Paul Siskind Fundamental Immunology Chapter 20 pp. 537–558.
Jonsson et al, Eur. J. of Clinical Microb & Infect Diseases, 1993 12: 289–293.
Consensus, *Paediatr. Infect. Dis. J.*, 8(1):S94–S97, 1989.
Murphy & Loeb, "Isolation of the Outer Membrane of *Branhamella catarrhalis*," *Microbial. Pathogenesis*, 6:159–174, 1989.
Murphy, T.F., "The Surfae of *Branhamella catarrhalis*: A Systemic Approach to the Surface Antigens of an Emerging Pathogen," *Paediatr. Infect. Dis. J.*, 8(1):S75–S77, 1989.
Murphy & Bartos, "Surface–Exposed and Antigenically Conserved Determinants of Outer Membrane Proteins of *Branhamella catarrhalis*," *Infect. Immun.*, 57(1):2938–2941, 1989.

Eliasson, I., "A Protein Antigen Characteristic of *Branhamella catarrhalis*," *Acta Path. Microbiol. Scand. Sect. B.*, 88:281–286, 1980.
Dialog Search Report.
Beaulieu & Roy, "Construction of a Species–Specific DNA Probe for *Branhamella catarrhalis*," 89th Annual Meeting of the American Society for Microbiology, New Orleans, LA, USA, May 14–18, 1989. *Abstr. Annu. Meet. Am. Soc. Microbiol.*, 89(0), 1989, p. 124, Abstract #D–249.
Bhushan & Murphy, "Molecular Characterization of Outer Membrane Protein E. of *Branhamella catarrhalis*: A Potential Vaccine Candidate," 91st General Meeting of the American Society for Microbiology 1991, Dallas, Texas, USA, May 5–9, 1991, *Abstr. Gen. Meet. Am. Soc. Microbiol.*, 91(0), 1991, p. 57, Abstact #B–191.
Black & Wilson, "Immunoglobulin G (IgG) Serological Response to *Branhamella catarrhalis* in Patients with Acute Bronchopulmonary Infections," *J. Clin. Pathol.*, 41:329–333, 1988.
Chapman et al., "Development of Bactericidal Antibody During *Branhamella catarrhalis* Infection," *J. of Infect. Dis.*, 151(5):878–882, 1985.
Helminen et al., "Molecular Cloning of a Gene Encoding a Surface–Exposed Outer Membrane Protein of *Moraxella Catarrhalis*," Abstract of the 1991 ICAA; 31 (O), p. 145, Abstract No. 278.
International Search Report, mailed Nov. 27, 1992.
Hanson, M.S. et al., "Expression of the Heat–Modifiable Major Outer Membrane Protein of *Haemophilus influenzae* Type b is Unrelated to Virulence," *Infection and Immunity*, 57(6):1639–1646, 1989.
Klingman, K.L. and Murphy, T.F., "Identification and Purification of the Lipooligosaccharide–Associated High Molecular Weight Outer Membrane Protein (HMW–OMP) of *Branhamella catarrhalis*," Abstract of the 92nd General Meeting of the American Society for Microbiology, p. 90, B–388, 1992.

(List continued on next page.)

*Primary Examiner*—Hazel F. Sidberry
*Attorney, Agent, or Firm*—Arnold White & Durkee

[57] ABSTRACT

The present disclosure relates to *Moraxella catarrhalis* outer membrane vesicle (OMV) compositions, to selected antigenic proteins from the outer membranes of *M. catarrhalis* which have a variety of useful properties, and to monoclonal antibodies against these proteins. Particular "Outer Membrane Proteins" (OMPs) of the invention are characterized as having molecular weights of about 30 kD, 80 kD (also termed CopB protein) and between about 200 and 700 kD (HMWP antigen). Passive immunization with monoclonal antibodies directed against these proteins confers protection against homologous and heterologous *Moraxella catarrhalis* strains in animal models, and active immunization with outer membrane vesicles also enhances pulmonary clearance of distinct *M. catarrhalis* strains. This demonstrates both the utility of antibodies in conferring passive immunity and the usefulness of OMPs, or variants thereof, in the preparation of vaccines. Also disclosed are DNA segments encoding these OMPs, methods for preparing the antigens, or variants, through the application of recombinant DNA techniques, as well as diagnostic methods and related embodiments.

11 Claims, 17 Drawing Sheets

OTHER PUBLICATIONS

Shenep, J.L., et al., "Further Studies of the Role of Noncapsular Antibody in Protection Against Experimental *Haemophilus influenzae* Type b Bacteremia," *Infection and Immunity*, 42(1): 257–263, 1983.

Srikumar, R., et al., "Monoclonal Antibodies Specific to Porin of *Haemophilus influenzae* Type b: Localization of Their Cognate Epitopes and Tests of Their Biological Activities," *Molecular Microbiology*, 6(5):665–676, 1992.

Yogev, R. and Hansen, E.J., "Disassociation of Virulence and Protection from Infection by Mutant Analysis in *Haemophilus influenzae* Type b," *Infection and Immunity*, 55(8):1944–1947, 1987.

Barinaga, "New Technique Offers a Window on Bacteria's Secret Weapons," *Science*, 259:595, 1993.

Chi et al., "Antibody Response to P–Protien in Pateints with *Branhamella catarrhalis* Infections," *The American Journal of Medicine*, 88 (suppl.5A):5A–25S, 1990.

Eliasson, "A Protein Antigen Characteristic of *Branhamella Catarrhalis,*" *Acta Path. Microbiol. Scand. Sect. B*, 88:281–286, 1980.

Hanson et al., "Expression of the Heat–Modifiable Major Outer Membrane Protein of *Haemophilus influenzae* Type b Is Unrelated to Virulence," *Infection and Immunity*, 57(6):1639–1646, 1989.

Mahan et al., "Selection of Bacterial Virulence Genes That Are Specifically Induced in Host Tissues," *Science*, 259:686–388, 1993.

Rustici et al., "Molecular Mapping and Detoxification of the Lipid A Binding Site by Synthetic Peptides," *Science*, 259:361–364, 1993.

Zollinger et al., "Safety and Immunogenicity of a *Neisseria meningitidis* Type 2 Protein Vaccine in Animals and Humans," *The Journal of Infectious Diseases*, 137(6):728–739, 1978.

Zollinger et al., "Complex of Meningococcal Group B Polysaccharide and Type 2 Outer Membrane Protein Immunogenic in Man," *The Journal of Clinical Investigation*, 63:836–848, 1979.-

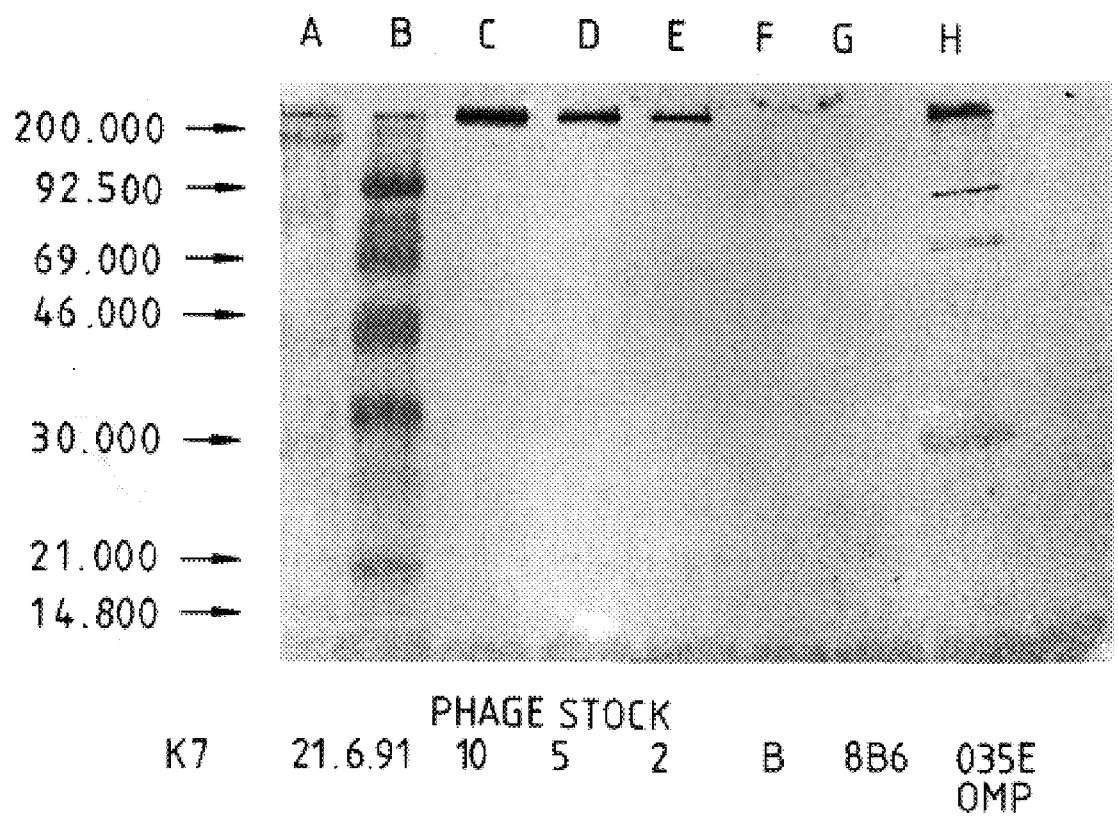

FIG. 7
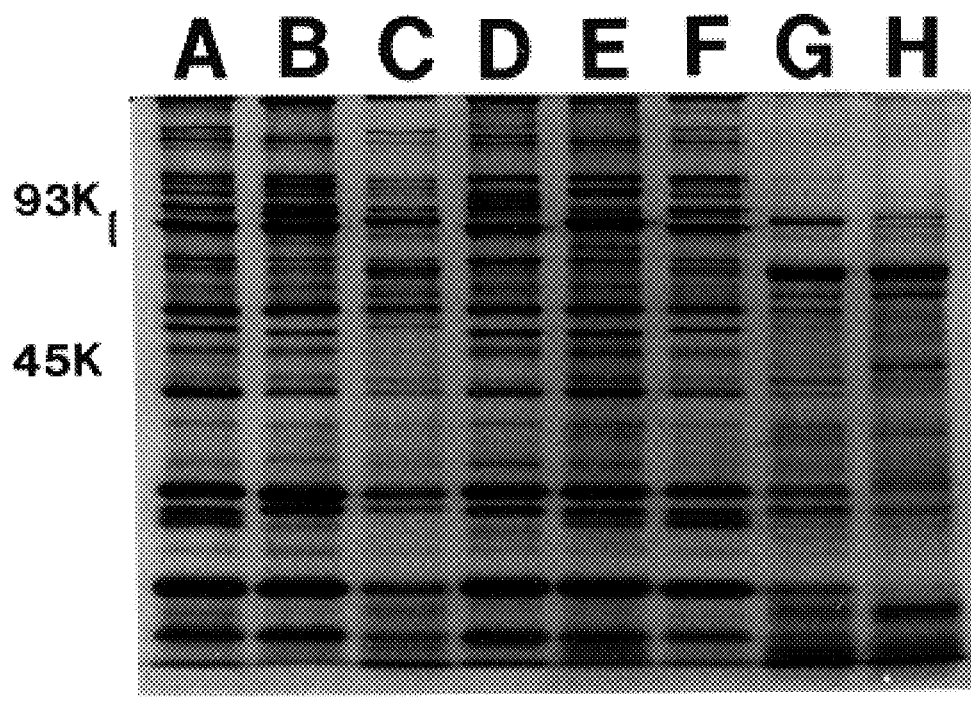
1
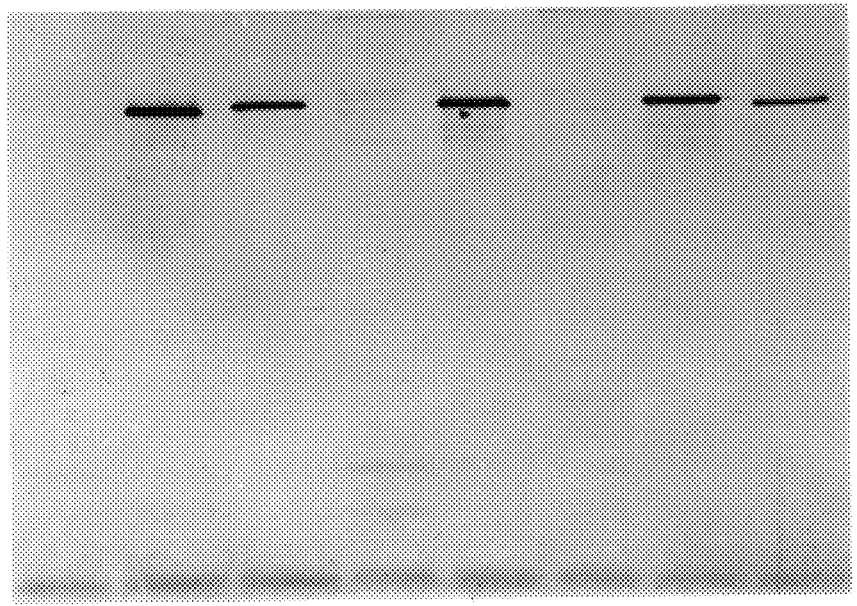
2

FIG. 10A

```
TCAATAAGTT GGAGTCATTA CCTGATTTTA GTAAGTAGAT GAGCAAGGGA TAATTTGACA        60

AAAACAAATT TGATTTCAAG CCTCATAATC GGAGTTATT ATG AAT AAG TTT CAA         114
                                             MET Asn Lys Phe Gln

TTA TTA CCG CTG ACA TTG GCG GTG AGT GCC GCT TTT ACA ACC ACT GCT        162
Leu Leu Pro Leu Thr Leu Ala Val Ser Ala Ala Phe Thr Thr Thr Ala

TTT GCA GCT GTT AGC CAG CCT AAG GTT GTC TTG GCA GGC GAT ACA GTG        210
Phe Ala Ala Val Ser Gln Pro Lys Val Val Leu Ala Gly Asp Thr Val

GTC AGT GAT CGC CAA GGT GCA AAA ATT AAA ACC AAT GTT GTT ACC TTA        258
Val Ser Asp Arg Gln Gly Ala Lys Ile Lys Thr Asn Val Val Thr Leu

CGA GAA AAA GAC GAA AGC ACG GCT ACA GAT TTG CGT GGT TTG TTA CAA        306
Arg Glu Lys Asp Glu Ser Thr Ala Thr Asp Leu Arg Gly Leu Leu Gln

GAT GAA CCT GCC ATC GGT TTT GGC GGT GGT TTT GGT ACT TCT CAA TTT        354
Asp Glu Pro Ala Ile Gly Phe Gly Gly Gly Phe Gly Thr Ser Gln Phe

ATC AGC ATT CGT GGC ATG GGT CAT AAT GCC ATT GAC CTA AAA ATT GAC        402
Ile Ser Ile Arg Gly Met Gly His Asn Ala Ile Asp Leu Lys Ile Asp
```

FIG. 10B

```
AAC GCT TAT CAA GAT GGT CAA TTA CAC TAC CAC CAA GGT CGC TTT ATG    450
Asn Ala Tyr Gln Asp Gly Gln Leu His Tyr His Gln Gly Arg Phe Met

CTA GAC CCC CAG ATG GTC AAA GTC GTT TCG GTA CAA AAA GGG GCA GGC    498
Leu Asp Pro Gln Met Val Lys Val Val Ser Val Gln Lys Gly Ala Gly

TTT GCC AGT GCA GGC ATT GGG GCA ACC AAT GGT GCG ATT GTT ACC AAA    546
Phe Ala Ser Ala Gly Ile Gly Ala Thr Asn Gly Ala Ile Val Thr Lys

ACC TTA GAT GCT GAT GAG CTT TTA AGA AAC AGC GAC AAA GAT TAT GGC    594
Thr Leu Asp Ala Asp Glu Leu Leu Arg Asn Ser Asp Lys Asp Tyr Gly

TTT AAA GTT GGT GCA GGC TTA TCA ACC AAC AAA GGT CAT TCT TAT CAT    642
Phe Lys Val Gly Ala Gly Leu Ser Thr Asn Lys Gly His Ser Tyr His

GGT AGT GCC TTT GGT AAA GCA CAG ACA GGA TTT GGT CAG GTA GAT GCC    690
Gly Ser Ala Phe Gly Lys Ala Gln Thr Gly Phe Gly Gln Val Asp Ala

CTT GTC TCT TAT AAT CAA GTA AAT GAC AGC GAC TAT AAA GGC GGT AAA    738
Leu Val Ser Tyr Asn Gln Val Asn Asp Ser Asp Tyr Lys Gly Gly Lys

GGG TAC ACC AAT CTG TTG GGC AAT GAT GTG GTT ACA AGA AGT GCC TTG    786
Gly Tyr Thr Asn Leu Leu Gly Asn Asp Val Val Thr Arg Ser Ala Leu
```

FIG. 10C

```
GAT AAA TCC AGT TAC CTT GTC AAG GCA GGG CTA ACT GCT GGC GAT CAT
Asp Lys Ser Ser Tyr Leu Val Lys Ala Gly Leu Thr Ala Gly Asp His    834

CGA TTT GTG GTC AGC CAT CTA AAT GAA GTT CAT AAA GGC ATT CGT GGC
Arg Phe Val Val Ser His Leu Asn Glu Val His Lys Gly Ile Arg Gly    882

GTG CGT GAA GAG TTT GAC TTC GCC AAT CGT GCC TTG ACG CTA GAT ATA
Val Arg Glu Glu Phe Asp Phe Ala Asn Arg Ala Leu Thr Leu Asp Ile    930

GAA AAA GAT AAG AAA AAA CGT ACT GAC GAA CAG CTT CAG GCA GAG TTA
Glu Lys Asp Lys Lys Lys Arg Thr Asp Glu Gln Leu Gln Ala Glu Leu    978

GAT AAC AAA TAT GCA GGC AAG GGT TAC AAA CTT GGC AGT AAA ACA CCA
Asp Asn Lys Tyr Ala Gly Lys Gly Tyr Lys Leu Gly Ser Lys Thr Pro   1026

GAT GGT AAA AAG TAT AAT GTG GTT GAT GCC AAT GGT AAA TTG GTG GCT
Asp Gly Lys Lys Tyr Asn Val Val Asp Ala Asn Gly Lys Leu Val Ala   1074

GAT TTA GAT AGG AAC AAC AAC CCA ACT CAG CGT GAA ACC TAC CAA AAG TTA
Asp Leu Asp Arg Asn Asn Asn Pro Thr Gln Arg Glu Thr Tyr Gln Lys Leu   1122

ACC AAC CTT GAA TGG ACA GGT AAA AAC CTT GGT TTT GCA AAT GAA GTT
Thr Asn Leu Glu Trp Thr Gly Lys Asn Leu Gly Phe Ala Asn Glu Val   1170
```

FIG. 10D

```
ACT GCC AAT GTC TAT AAG TTA GAA CAT GGA CGC AAC TCC TCT AGC GAT    1218
Thr Ala Asn Val Tyr Lys Leu Glu His Gly Arg Asn Ser Ser Ser Asp

AAA GGT AAC AGC TAT ATT CTT CGT GAT GTA CCT AAT ACC ATC AAT GAT    1266
Lys Gly Asn Ser Tyr Ile Leu Arg Asp Val Pro Asn Thr Ile Asn Asp

AAC GGT GAT AGC CCA TCA AAT ATG CAT GTG GTA GCC ACA GGG GCT AAT    1314
Asn Gly Asp Ser Pro Ser Asn Met His Val Val Ala Thr Gly Ala Asn

ATT AAT TTT GAT AAA GAA TTT AAT CAC GGT CTA TTA AAA GGC TTT GGC    1362
Ile Asn Phe Asp Lys Glu Phe Asn His Gly Leu Leu Lys Gly Phe Gly

GTT GAC CAT ACT TTA TTA AAA TAT GGC ATC AAC TAT CGC CAT CAA GAA    1410
Val Asp His Thr Leu Leu Lys Tyr Gly Ile Asn Tyr Arg His Gln Glu

GCT GTA CCG CCT AGA GGT ATT AGA CCT GGT TTT CAA AAC CAA GAA AAA    1458
Ala Val Pro Pro Arg Gly Ile Arg Pro Gly Phe Gln Asn Gln Glu Lys

ACC GAT GCT GGC ATT TAT CTA GAA GCG GTT AAC CAA ATC AAT GAC TTT    1506
Thr Asp Ala Gly Ile Tyr Leu Glu Ala Val Asn Gln Ile Asn Asp Phe

ACC ATC AAT ACA GGC GTG CGT GTT GAC CGT TTT AAA GCT ATG           1554
Thr Ile Asn Thr Gly Val Arg Val Asp Arg Phe Lys Ala Met
```

FIG. 10E

```
GAC GGT AAA AAG GTT GGA AAA ACC GAC ATC AAC CCA AGC TTT GGG GTG    1602
Asp Gly Lys Lys Val Gly Lys Thr Asp Ile Asn Pro Ser Phe Gly Val

ATT TAT GAT GTC AAT CCT AAT CTT AGC GTC AGC GGT AAC CTA ATC TAT    1650
Ile Tyr Asp Val Asn Pro Asn Leu Ser Val Ser Gly Asn Leu Ile Tyr

GCC ACT CGC AGC CCA CGC TTT GCT GAT GCT ATC CTA AGC CGT GGC TTC    1698
Ala Thr Arg Ser Pro Arg Phe Ala Asp Ala Ile Leu Ser Arg Gly Phe

CGT GAT GGC GTT GTG AGT ATT GCT GAT AAC GCA AAA GCA GAA AAA GCA    1746
Arg Asp Gly Val Val Ser Ile Ala Asp Asn Ala Lys Ala Glu Lys Ala

CGC AAT ACC GAG ATT GGT TTT AAC TAT AAT GGG CCA TAT ACC GCC        1794
Arg Asn Thr Glu Ile Gly Phe Asn Tyr Asn Gly Pro Tyr Thr Ala

TTT GGC AGC TAT TTT TGG CAG CGT GTG GAT AAT GCC AGA GCT ACT GCC    1842
Phe Gly Ser Tyr Phe Trp Gln Arg Val Asp Asn Ala Arg Ala Thr Ala

GAT GCT GTA CAA CAC CCC ACA GTT ACA ACA GCT AAG ATT ACC TAT CTT    1890
Asp Ala Val Gln His Pro Thr Val Thr Thr Ala Lys Ile Thr Tyr Leu

GGC AAC CAA GGT CAT CAG ACC AAC CAC GGT TAT GAG CTG GGC GTA GGC    1938
Gly Asn Gln Gly His Gln Thr Asn His Gly Tyr Glu Leu Gly Val Gly
```

FIG. 10F

```
TAT ACC GAA GGT GCG TGG CGT GCG CGT GCT GGC GTT GCT CAC AGC AAG      1986
Tyr Thr Glu Gly Ala Trp Arg Ala Arg Ala Gly Val Ala His Ser Lys

CCA ACC ATG CAC AAT GTC AAA TTT AAA GCC AAC CCT GAA TAT GCC GTG      2034
Pro Thr Met His Asn Val Lys Phe Lys Ala Asn Pro Glu Tyr Ala Val

CGT ACA GGT CGT ACA TGG ACA GCA GAT GTC GCC TAT CGC CTG CCA AAC      2082
Arg Thr Gly Arg Thr Trp Thr Ala Asp Val Ala Tyr Arg Leu Pro Asn

CCC AGT GTA GAG CTT GGT GTG AGA CAC ACA TTG GTT GAA GGG GTA GAT      2130
Pro Ser Val Glu Leu Gly Val Arg His Thr Leu Val Glu Gly Val Asp

GCC AAA GAC ACT TCT ATC CTT AGC GGT AAA TTT GAT GAT AAA GAT GGT      2178
Ala Lys Asp Thr Ser Ile Leu Ser Gly Lys Phe Asp Asp Lys Asp Gly

GCT ATT CTT AAC CGT GAA GGC TAT AAT GTC AGT GAC ATC TAT GCC AAC      2226
Ala Ile Leu Asn Arg Glu Gly Tyr Asn Val Ser Asp Ile Tyr Ala Asn

TGG AAG CCT TAT GGC AAT GAT AAG GTA AAC TTT GCG GTG AAT              2274
Trp Lys Pro Tyr Gly Asn Asp Lys Val Asn Phe Ala Val Asn

AAT GTC TTT AAT AAA AAC TAT CGC CCA CAC ACT CAG CGT GCT TCC ATA      2322
Asn Val Phe Asn Lys Asn Tyr Arg Pro His Thr Gln Arg Ala Ser Ile
```

FIG. 10G

```
GAT ACC TTA CCT GGG GCA GGT CGT GAT TTC CGT GTT GGC GTG AAC TTC    2370
Asp Thr Leu Pro Gly Ala Gly Arg Asp Phe Arg Val Gly Val Asn Phe

ACT TAC TAATACTTGC CGATTTATCG GTATAATACT GAACACTCAA GCACGCTTGG     2426
Thr Tyr

GTGTTCTTTT TATGGGTATG AGTGGATAAA AACGATAAAA AAAGCCAATC GTATCATATT  2486

GATTGGCTAT AATGATAAAA TTAAAATCATT ACTG                             2520
```

A B C

D E F

METHODS AND COMPOSITIONS RELATING TO USEFUL ANTIGENS OF *MORAXELLA CATARRHALIS*

This application is a continuation-in-part of copending PCT application, U.S. Ser. No. 92/06869, filed Aug. 14, 1992, which was a continuation-in-part of U.S. Ser. No. 07/745,591, filed Aug. 21, 1991 now U.S. Pat. No. 5,552, 146.

The government owns certain rights in the present invention pursuant to NIH grant number AI 23366.

BACKGROUND OF THE INVENTION

1. Field of the Invention

The present invention relates generally to various outer membrane proteins (OMPs) of *Moraxella catarrhalis* for use as targets in immunotherapy, such as in the preparation of vaccines or protective antibodies for use in treatment of *Moraxella catarrhalis*-related diseases. In particular aspects, the present invention concerns antigens identified by molecular weights of about 30 kD, 80 Kd (CopB) and a third antigen, termed "high molecular weight protein" or "HMWP" antigen having a molecular weight of between about 200 and 700 kD, as measured by SDS-polyacrylamide gel electrophoresis. In other aspects, the invention concerns recombinant clones and DNA segments encoding *M. catarrhalis* antigens and fragments and equivalents thereof, as well as to antibodies reactive with these species. Further, the invention concerns methods for the detection of *M. catarrhalis* antigens and antibodies, as well as the use of specific antigens and antibodies both in passive and active immunity against *M. catarrhalis* infections.

2. Description of the Related Art

It was previously thought that *Moraxella catarrhalis* (previously known as *Branhamella catarrhalis* or *Neisseria catarrhalis*) was a harmless saprophyte of the upper respiratory tract (Catlin, 1990; Berk, 1990). However, during the previous decade, it has been determined that this organism is an important human pathogen. Indeed, it has been established that this Gram-negative diplococcus is the cause of a number of human infections (Murphy, 1989). *M. catarrhalis* is now known to be the third most common cause of both acute and chronic otitis media (Catlin, 1990; Faden et al., 1993;1991; Marchant, 1990), the most common disease for which infants and children receive health care (Consensus, 1989). This organism also causes acute maxillary sinusitis, generalized infections of the lower respiratory tract (Murphy & Loeb, 1989), and is an important cause of bronchopulmonary infections in patients with underlying chronic lung disease and, less frequently, of systemic infections in immunocompromised patients (Melendez & Johnson, 1990; Sarubbi et al., 1990; Schonheyder & Ejlertsen, 1989; Wright & Wallace, 1989).

The "Consensus" report referred to above concluded that prevention of otitis media is an important health care goal due to both its occurrence in infants and children, as well as certain populations of all age groups. In fact, the total financial burden of otitis media has been estimated to be at least 2.5 billion annually, or approximately 3% of the health care budget. Vaccines were identified as the most desired approach to the prevention of this disease for a number of reasons. For example, it was estimated that if vaccines could reduce the incidence of otitis media by 30%, this outcome could bring about an annual health care savings of at least $400 million. However, while some progress has been made in the development of vaccines for 2 of the 3 common otitis media pathogens, *Streptococcus pneumoniae* and *Haemophilus influenzae*, there is no indication that similar progress has been made with respect to *M. catarrhalis*. This is particularly troublesome in that *M. catarrhalis* now accounts for approximately 17–20% of all otitis media infection (Murphy, 1989).

Previous attempts have been made to identify and characterize *M. catarrhalis* antigens that would serve as potentially important targets of the human immune response to infection (Murphy, 1989; Goldblatt et al., 1990; Murphy et al., 1990). Generally speaking, the surface of *M. catarrhalis* is composed of outer membrane proteins (OMPs), lipooligosaccharide (LOS) and fimbriae. As Murphy points out, *M. catarrhalis* appears to be somewhat distinct from other gram-negative bacteria in that attempts to isolate the outer membrane of this organism using detergent fractionation of cell envelopes has generally proven to be unsuccessful in that the procedures did not yield consistent results (Murphy, 1989; Murphy & Loeb, 1989). Moreover, preparations were found to be contaminated with cytoplasmic membranes, suggesting an unusual characteristic of the *M. catarrhalis* cell envelope.

More recently, isolation procedures have been reported for obtaining *M. catarrhalis* outer membrane components which result in what are said to be less-contaminated membrane preparations (Murphy & Loeb, 1989). Although this has allowed *M. catarrhalis* outer membrane protein profiles to be assessed by sodium dodecyl sulfate polyacrylamide gel electrophoresis (SDS/PAGE), these techniques did not lead to the isolation or characterization of OMPs (Murphy & Loeb, 1989). Indeed, information regarding individual OMPs is still limited to their apparent molecular weight on SDS/PAGE, with protein bands on SDS gels being grouped into general classes (Murphy & Loeb, 1989; Murphy, 1989). Seven or eight major OMP groups have been identified in this manner and appear to be fairly consistent between diverse *M. catarrhalis* strains. For example, OMPs have been grouped into classes A–H, beginning with bands of molecular weight around 98 kD (OMP-A) and proceeding to bands with molecular weights of about 21 kD (OMP-H) (Murphy & Loeb, 1989; Murphy, 1989).

The LOS of *M. catarrhalis* has also been suggested as a possible target for vaccine development. LOS has been isolated from *M. catarrhalis* strains and subjected to SDS-PAGE and silver staining (Murphy, 1989). In common with the OMPs, the LOS of *M. catarrhalis* appears to be fairly well conserved at the antigenic level (Vaneechoutte et al., 1990), thus raising the feasibility of using a portion of the LOS molecule as a vaccine component.

Lastly, the Fimbriae have been suggested as a possible vaccine candidate. Fimbriae apparently play a role in adherence and colonization of mucosal services in some bacteria. Workers in the field have postulated that if antigenically conserved epitopes are expressed on fimbriae and can be identified, then it is possible that antibodies to such epitopes might be useful therapeutically, or that such epitopes can serve as vaccine components.

Despite its recognized virulence potential, little is known about the mechanisms employed by *M. catarrhalis* in the production of disease or about host. factors governing immunity to this pathogen. An antibody response to *M. catarrhalis* otitis media has been documented by means of an ELISA system using whole *M. catarrhalis* cells as antigen and acute and convalescent sera or middle ear fluid as the source of antibody (Leinonen et al., 1981). The development of serum bactericidal antibody during *M.* catarrhalis infection in adults was first reported nearly a decade ago and this bactericidal activity was shown to be dependent on the classical complement pathway (Chapman et al., 1985). Most recently, it was reported that young children with *M. catarrhalis* otitis media develop an antibody response in the middle ear but fail to develop systemic antibody in a uniform manner (Faden et al., 1992).

With the rising importance of this pathogen in respiratory tract infections, identification of the surface components of this bacterium involved in virulence expression and immunity is becoming more important. Unfortunately, the lack of a suitable animal model with which to study *M. catarrhalis* middle ear infections has further hampered such investigations. The relative lack of virulence of this organism for animals has rendered identification of an appropriate model system difficult (Doern, 1986). Attempts to use rodents, including chinchillas, to study middle ear infections caused by *M. catarrhalis* were unsuccessful, likely because this organism cannot grow or survive in the middle ear of these hosts (Doyle, 1989).

Although various subcomponents of the *M. catarrhalis* cell have been suggested as places to begin a search for vaccine candidates, there has still been no such candidate identified. No antigenic epitope or epitopes have been shown to induce protective antibodies. Thus, it is clear that there is currently a need to identify *M. catarrhalis* component(s) which may serve as useful antigens and which can, for example, be employed in the preparation of both passive and active immunotherapeutic reagents such as vaccines. Additionally, once such an antigen or antigens is identified, there is a need for providing methods and compositions which will allow the preparation of these vaccines and quantities that will allow their use on a wide scale basis in therapeutic protocols.

SUMMARY OF THE INVENTION

Accordingly, in a general and overall sense, the present invention is concerned with the identification and subsequent preparation of an *Moraxella catarrhalis* antigen species that would be of use both in the prevention and diagnosis of disease. In more particular terms, the invention concerns the inventors' surprising discovery that *M. catarrhalis* outer membrane vesicles (OMVs) and certain *M. catarrhalis* OMP antigens, including the 30 kD, 80 kD (CopB) and HMWP OMP antigens, have particular utility in vaccine development. It is postulated by the inventors, therefore, these antigens can be used directly as a component of a vaccine, or can be employed for the preparation of corresponding or equivalent antigen through sequence analysis. Particularly preferred embodiments of the invention concern DNA segments and vectors encoding the 30 kD, 80 kD (CopB) and HMWP OMP antigens and related species, antibodies recognizing these antigen species, methods for protecting against *M. catarrhalis* challenge using the antigen compositions and/or antibodies disclosed herein, and the like.

In certain embodiments, the 30 kD and HMWP OMP antigens are considered to be particularly useful. Antibodies directed against these two OMP species are shown to be broadly reactive with *M. catarrhalis* subtypes and isolates, and mice passively immunized with Mab 17C7, against the HMWP antigen, exhibit an enhanced ability to clear both homologous and heterologous *M. catarrhalis* strains from their lungs. However, the 80 kD antigen, termed CopB, is also envisioned to be a particularly useful vaccine candidate. This is evidenced by monoclonal antibodies against CopB (10F3) reacting with the majority (about 70%) of *M. catarrhalis strains*, the use of polyclonal antisera to demonstrate antigenic cross-reactivity of *M. catarrhalis* CopB proteins, copB-like structural genes being present in seven out of eight different strains, and the ability of anti-CopB antibodies to enhance clearance of *M. catarrhalis* strains from the lungs of mice.

The present invention concerns antigen compositions, free from total *M. catarrhalis* cells, which comprise purified *M. catarrhalis* outer membrane antigens. One example of such an antigen composition is *M. catarrhalis* outer membrane vesicles themselves. Further antigen compositions of the invention comprise purified protein or peptide antigen(s) which incorporate an epitope that is immunologically cross-reactive with one or more *M. catarrhalis* OMP antigens, and particularly with the 80 kD (CopB) OMP. Generally, the purified protein or peptide antigen will comprise the OMP itself. Accordingly, the invention particularly embodies a purified *M. catarrhalis* 80 kD CopB outer membrane protein, and preferably, a recombinant purified *M. catarrhalis* 80 kD CopB OMP, as obtained from a recombinant host cell. In addition, the present disclosure also provides techniques which may be employed for preparing variants of these OMP antigens, including, for example, peptides that incorporate related antigenic epitopes, epitopic core sequence peptides of between about 15 to about 50, or preferably, about 15 to about 30, amino acids in length, as well as antigenic functional equivalents of each of these.

Furthermore, in that DNA segments encoding the various OMP antigens are disclosed, the antigens may be provided essentially free of antigenic epitopes from other *M. catarrhalis* antigens through the application of recombinant technology. That is, one may prepare the antigen by recombinant expression means using a host cell other than *M. catarrhalis* or related species, and thereby provide the antigen in an essentially pure antigenic state with respect to other *M. catarrhalis* antigens. Such preparations will therefore be free, e.g., of LOS or fimbriae antigens.

In still further embodiments, through the use of standard DNA sequencing technology, DNA segments disclosed herein may be sequenced, and from this DNA sequence one may determine the underlying amino acid sequence of the selected OMP protein, whether it be the 30 kD, 80 kD or HMWP OMP species. Once this information is obtained, for example, as has been determined for the 80 kD antigen termed CopB, the identification of suitable antigenic epitopes is a relatively straightforward matter. This can be achieved through the use of, for example, software programs for the prediction of such epitopes that are available to those of skill in the art. The amino acid sequence of these "epitopic core sequences" may then be readily incorporated into shorter peptides, either through the application of peptide synthesis or recombinant technology.

Preferred peptides will generally be on the order of 15 to 50 amino acids in length, and more preferably about 15 to about 30 amino acids in length. It is proposed that shorter antigenic peptides which incorporate epitopes of the selected OMP will provide advantages in certain circumstances, for example, in the preparation of vaccines or in immunologic detection assays. Exemplary advantages include the ability to circumvent problems of contamination and purity often associated with proteins prepared by recombinant production in that peptides of this length may be prepared readily be synthetic means using peptide synthesizers.

In other embodiments, the present invention concerns processes for preparing compositions which include purified protein or peptide antigens that incorporate epitopes that are immunologically cross-reactive with the 30 kD, 80 kD (CopB) or HMWP OMP. In a general sense, these processes include first selecting cells that are capable of expressing such a protein or peptide antigen, culturing the cells under conditions effective to allow expression of the antigen, and collecting the antigen to thereby prepare the composition. Where one desires to prepare the OMP antigen itself, one will simply desire to culture *M. catarrhalis* cells as a first step. In this case, the antigen will be provided, upon expression, in the outer membrane fraction of the cell. The antigen is then prepared by, first, preparation of membrane fraction followed by solubilization and extraction of the antigen from the prepared membranes using an ionic or non-ionic detergent. Further purification may be achieved by a variety of methods including column fractionation, isoelectric focusing, and the like, or even immunoadsorption employing OMP-directed antibodies.

As used herein, the term "incorporating an epitope(s) that is immunologically cross-reactive with the 30 kD, 80 kD (CopB) or HMWP OMP" is intended to refer to a peptide or protein antigen which includes a primary, secondary or tertiary structure similar to an epitope located within the 30 kD, 80 kD (CopB) or HMWP OMPs. The level of similarity will generally be to such a degree that monoclonal or polyclonal antibodies directed against the 30 kD, 80 kD (CopB) or HMWP OMPs will bind to, react with, or otherwise recognize, the cross-reactive peptide or protein antigen. Preferred methods for assessing cross-reactivity are contemplated to include, but are not limited to, methods using the monoclonal antibodies of the present invention, namely MAb 8B6 (ATCC HB 11091), directed against the 30 kD OMP; MAb 17C7 (ATCC HB 11093), directed against the HMWP OMP; and particularly, MAb 10F3 (ATCC HB 11092), directed against the 80 kD (CopB) OMP. Various immunoassay methods may be employed in conjunction with such antibodies, such as, for example, Western blotting, ELISA, RIA, and the like, all of which are known to those of skill in the art.

Of course, in light of the disclosure herein one may choose more preferred embodiments to prepare the desired antigen that include expressing a recombinant DNA segment encoding the antigen in a recombinant host cell. Preferred recombinant host cells for expression of antigens in accordance with the invention will typically be a bacterial host cell in that the antigen is a bacterial antigen. Preferred bacterial host cells include *E. coli, H. influenzae*, Salmonella species, Mycobacterium species, or even *Bacillis subtilis* cells. Of course, where desired, one may also express the desired antigen or antigens in eukaryotic cells.

As indicated above, in particular embodiments, the present invention concerns DNA segments which encode the desire protein or peptide antigen. Methods are disclosed herein for obtaining such segments in a purified state relative to their naturally occurring state. These DNA segments will have a number of advantages and uses. For example, segments encoding the entire OMP gene may be introduced into recombinant host cells and employed for expressing the entire protein antigen. Alternatively, through the application of genetic engineering techniques, subportions or derivatives of the selected OMP gene may be employed to prepare shorter peptide sequences which nevertheless incorporate the desired antigenic epitopes. Furthermore, through the application of site-directed mutagenesis techniques, one may re-engineer DNA segments of the present invention to alter the coding sequence, e.g., to introduce improvements to the antigenicity of epitopic core sequences and thereby prepare antigenically functional equivalent peptides. Of course, where desired, one may also prepare fusion peptides, e.g., where the antigen coding regions are aligned within the same expression unit with other desired antigen or proteins or peptides having desired functions, such as for immunodetection purposes (e.g., enzyme label coding regions).

The present invention is particularly directed to DNA segments encoding the 80 kD antigen termed CopB and portions thereof. As used herein, the term "DNA segment" is intended to refer to a DNA molecule which has been isolated free of total genomic DNA of a particular species. Therefore, a DNA segment encoding the 80 kD or CopB antigen refers to a DNA segment which contains such coding sequences yet is isolated away from total *M. catarrhalis* genomic DNA. Included within the term "DNA segment", are DNA segments which may be employed in the preparation of vectors, as well as the vectors themselves, including, for example, plasmids, cosmids, phage, viruses, and the like.

In certain embodiments, the present invention concerns isolated DNA segments and recombinant vectors incorporating DNA sequences which encode an *M. catarrhalis* 80 kD or CopB antigen that includes within its amino acid sequence the amino acid sequence of seq id no:2. Recombinant vectors and isolated segments may variously include an *M. catarrhalis* CopB antigen coding region alone, a coding region bearing selected alterations or modifications in the basic coding region, or may encode larger polypeptides which nevertheless include sequences which encode polypeptides capable of immunologically cross-reacting with an *M. catarrhalis* 80 kD CopB antigen.

Particularly useful recombinant vectors are contemplated to be those vectors in which the DNA segment encoding the *M. catarrhalis* CopB protein or peptide, antigen fragment, epitopic core sequence or variant thereof, is positioned under the control of a promoter. The promoter may be in the form of the promoter which is naturally associated with the CopB gene in *M. catarrhalis* cells, as; may be obtained by isolating the 5' non-coding sequences located upstream of the CopB coding segment or exon, for example, using recombinant cloning and/or PCR technology.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with the copB gene in its natural environment. Such promoters may include *M. catarrhalis* promoters normally associated with other genes, and/or promoters isolated from any other bacterial, eukaryotic, or mammalian cell. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the T7 RNA polymerase promoter system described by Tabor & Richardson (1985) and the maltose binding protein-fusion protein system (Guan et al., 1987; Nagai & Thogersen, 1987).

It will be understood that these aspects of the invention are not limited to the particular nucleic acid and amino acid sequences of seq id no:1 and no:2 respectively. Accordingly, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

Depending on the host system employed, one may find particular advantages where DNA segments of the present invention are incorporated into appropriate vector sequences which may, e.g., improve the efficiency of transfection of host cells. Where bacterial host cells are employed, it is proposed that virtually any vector known in the art to be appropriate for the selected host cell may be employed. Thus, in the case of E. Coli, one may find particular advantages through the use of plasmid vectors such as pBR322, or bacteriophages such as λGEM-11. Other particular examples are disclosed hereinbelow, and further examples will be known to those of skill in the art.

In the preparation of recombinant clone banks from which appropriately transfected cells are selected, it will generally be the case that expression of the selected OMP gene sequences can be achieved in such host cells without the use of vectors having their own intrinsic promoter sequences. This is because the genomic M. catarrhalis DNA fragments employed for clone bank preparation will include endogenous promoters associated with the various coding sequences. However, the inventors propose that one may ultimately desire to re-engineer the promoter region of the antigen-coding fragments of the present invention to introduce heterologous promoter. It is contemplated that this would allow one to "overexpress" the OMP antigen in relation to its natural expression in M. catarrhalis cells. Such overexpression may be assessed by a variety of methods, including radio-labelling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide, in comparison to the level in natural M. catarrhalis cells, is indicative of overexpression.

It is contemplated that nucleic acid segments of the present invention will have numerous uses other than in connection with expression of antigenic peptides or proteins. For example, nucleic acid segments of at least 10 to 20 or so nucleotides in length that incorporate regions of the OMP gene sequence may be employed as selective hybridization probes for the detection of M. catarrhalis sequences in selected samples or, e.g., to screen clone banks to identify clones which comprise corresponding or related sequences. Furthermore, short segments may be employed as nucleic acid primers, such as in connection with PCR technology, for use in any of a number of applications, including, e.g., cloning and engineering exercises, or in PCR-based detection protocols.

As is discussed more fully hereinbelow, nucleic acid molecules having OMP gene-complementary stretches of 20, 30, 50, or even of 100 nucleotides or so, will also have utility, for example as probes for use in a variety of hybridization embodiments such as Southern and Northern blotting in connection with various M. catarrhalis strains. The total size of fragment, as well as the size of the complementary stretch(es), will ultimately depend on thE intended use or application of the particular nucleic acid segment. Smaller fragments will generally find use in hybridization embodiments, wherein the length of the complementary region may be varied, such as between about 10 and about 100 nucleotides, according to the complementary sequences one wishes to detect.

Longer segments will often find particular utility in the recombinant production of peptides or proteins. DNA segments which encode peptide antigens from about 15 to about 50 amino acids in length, or more preferably, from about 15 to about 30 amino acids in length are contemplated to be particularly useful, as are DNA segments encoding the entire CopB antigen. DNA segments encoding peptides will generally have a minimum coding length in the order of about 45 to about 150, or about 90 nucleotides, whereas DNA segments encoding the full length copB protein will generally have a minimum coding length in the order of about 2520 nucleotides.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 basepairs in length, with segments of 5,000 or 3,000 being preferred and segments of about 1,000 basepairs in length being particularly preferred.

In still further embodiments, the invention concerns the preparation of antibodies capable of immunocomplexing with epitopes of the OMP antigen. Particular techniques for preparing antibodies in accordance with the invention are disclosed hereinbelow. However, it is proposed by the inventors that any of the current techniques known in the art for the preparation of antibodies in general may be employed, through the application of either monoclonal or polyclonal technology. The preparation of suitable monoclonal antibodies is disclosed herein and hybridomas which produce the preferred MAbs of the invention have also been deposited with the ATCC as follows: MAb 8B6 (ATCC HB 11091), directed against the 30 kD OMP; MAb 10F3 (ATCC HB 11092), directed against the 80 kD (CopB) OMP; and MAb 17C7 (ATCC HB 11093), directed against the HMWP OMP.

As noted above, a surprising aspect of the invention involves the discovery that monoclonal antibodies directed against the 30 kD, 80 kD) (CopB) and HMWP OMP antigens provide a protective effect against both homologous and heterologous M. catarrhalis challenge in animal models, as does immunization with M. catarrhalis outer membrane vesicles (OMVs). This unexpected finding indicates not only that antibodies may be employed in the preparation of compositions for use in connection with passive immunotherapy, but further, that antigen compositions comprising these OMP epitopes, including OMVs themselves, may be employed in the preparation of vaccines. Accordingly, the present invention is directed to pharmaceutical compositions such as vaccines which include firstly, an antigen in accordance herewith, whether obtained from recombinant or natural sources; or secondly, antibodies against such an antigen, together with a pharmaceutically acceptable carrier, diluent, or adjuvant.

The present invention is directed to vaccine compositions comprising purified *M. catarrhalis* outer membrane antigens, free from total *M. catarrhalis* cells, as exemplifed by purified protein or peptide antigens and by *M. catarrhalis* outer membrane vesicle (OMV) compositions. In certain aspects, the invention is directed to vaccine compositions comprising purified protein or peptide antigens which incorporate an epitope that is immunologically cross-reactive with the 80 kD (CopB) OMP, together with a pharmaceutically acceptable carrier, diluent or adjuvant. Certain vaccines compositions will include a purified *M. catarrhalis* 80 kD CopB outer membrane protein itself, and preferably a recombinant form of this protein, as obtained from a recombinant host cell. Vaccines comprising an *M. catarrhalis* OMV composition in combination with, or supplemented by, an *M. catarrhalis* 80 kD CopB outer membrane protein are also encompassed by the present invention.

In using *M. catarrhalis* OMVs or membrane protein preparations as the basis for, or as a part of, an antigen composition intended for use as a vaccine, it is contemplated that one would wish to first reduce, eliminate or de-toxify the endotoxin (lipopolysaccharide, LPS) within the composition. The preparation of compositions containing outer membrane proteins essentially free of endotoxin can be achieved by any one of the methods known to those of skill in the art, such as, for example, as disclosed in U.S. Pat. No. 4,271,147 (incorporated herein by reference) in connection with *Neisseria meningitidis*; and by reference to published articles such as those by Zollinger et al. (1978; 1979).

Methods for inducing tolerance to *M. catarrhalis* challenge in animals are also part of the present invention. Such methods generally comprise administering to the animal, or "immunizing the animal", with an immunologically effective amount of an antigen composition, such as a vaccine, prepared in accordance herewith. As mentioned above, the vaccine employed may include an *M. catarrhalis* OMV antigen composition with reduced-endotoxin levels; a purified protein or peptide antigen composition; an *M. catarrhalis* 80 kD CcpB outer membrane protein; or an 80 kD CopB OMP in addition to, or in combination with, a suitable *M. catarrhalis* OMV composition. A particular advantage of the invention is that it provides compositions which are effective against both homologous and heterologous *M. catarrhalis* strains, as evidenced by enhanced pulmonary clearance in animal models.

In still further embodiments, the present invention concerns immunodetection methods and associated kits. It is proposed that antigens of the present invention may be employed to detect antibodies having reactivity therewith, or, alternatively, antibodies prepared in accordance with the present invention, may be employed to detect antigens. In general, these methods will include first obtaining a sample suspected of containing such an antigen or antibody, contacting the sample with an antibody or antigen in accordance with the present invention, as the case may be, under conditions effective to allow the antibody to form an immunocomplex with the antigen or antibody to be detected, and detecting the presence of the antigen in the sample by detecting the formation of an immunocomplex.

In general, the detection of immunocomplex formation is quite well known in the art and may be achieved through the application of numerous approaches. For example, the present invention contemplates the application of ELISA, RIA, immunoblot, dotblot, indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For diagnostic purposes, it is proposed that virtually any sample suspected of comprising either the antigen or antibody sought to be detected, as the case may be, may be employed. Exemplary samples incluce clinical samples obtained from a patient such as blood or serum samples, ear swabs, sputum samples, middle ear fluid or even perhaps urine samples may be employed. Furthermore, it is contemplated that such embodiments may have application to non-clinical samples, such as in the titering of antigen or antibody samples, in the selection of hybridomas, and the like.

In related embodiments, the present invention contemplates the preparation of kits that may be employed to detect the presence of antigens and/or antibodies in a sample. Generally speaking, kits in accordance with the present invention will include a suitable OMP antigen (i.e., either the 30 kD, 80 kD (CopB) or HMWP species, or protein containing epitopes corresponding to one or more of these species), or antibody directed against such an antigen, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container means will generally include a vial into which the antibody, antigen or detection reagent may be placed, and preferably suitably aliquoted. The kits of the present invention will also typically include a means for containing the antibody, antigen, and reagent containers in close confinement for commercial sale. Such containers may include injection or blow-molded plastic containers into which the desired vials are retained.

BRIEF DESCRIPTION OF THE DRAWINGS

FIG. 5. Western blot analysis of *M. catarrhalis* proteins using as a probe monoclonal antibody 17C7, which recognizes the HMWP OMP. Lane A is a Rainbow protein molecular weight marker (M.W. 14.3 to 200 kD, Amersham); Lane B is a prestained SDS-PAGE-standard, low molecular weight (M.W. 16 to 110 kD, Bio-Rad); Lanes C, D and E contain proteins from a phage lysate of recombinant *E. coli* that express the HMWP OMP (LE392/17C7); Lane F is a blank control; Lane H is a negative control (phage lysate from recombinant *E. coli* expressing the 30 kD OMP, *E. coli*/8B6 phage lysate); and Lane G is a positive control (*M. catarrhalis* 035E outer membrane vesicles).

FIG. 7. Proteins present in outer membrane vesicles from eight strains of *M. catarrhalis* and their reactivity with Mab 10F3 in Western blot analysis. Outer membrane vesicles were resolved by SDS-PAGE and stained with Coomassie blue (panel 1) or transferred to nitrocellulose and probed with Mab 10F3 in Western blot analysis (panel 2). Lane A, strain B21; lane B, strain 035E, lane C, strain P44; lane D, strain P48; lane E, strain TTA1; lane F, strain TTA24; lane G, strain TTA37; lane H, strain W1. Molecular weight position markers are present on the left side of panel 1; the brackets on either side of panel 1 indicate the region in which the 80 kDa protein migrates.

FIG. 10. Nucleotide sequence of the copB gene (seq id no:1). A putative −35 consensus sequence is underlined at positions 55–60 and a putative Shine-Delgarno site is underlined at positions 91–94. The predicted amino acid sequence of the CopB protein (seq id no:2) is shown beneath the nucleotide sequence. The proposed leader peptide is underlined at positions 100–168.

DETAILED DESCRIPTION OF THE PREFERRED EMBODIMENTS

Figure 1:
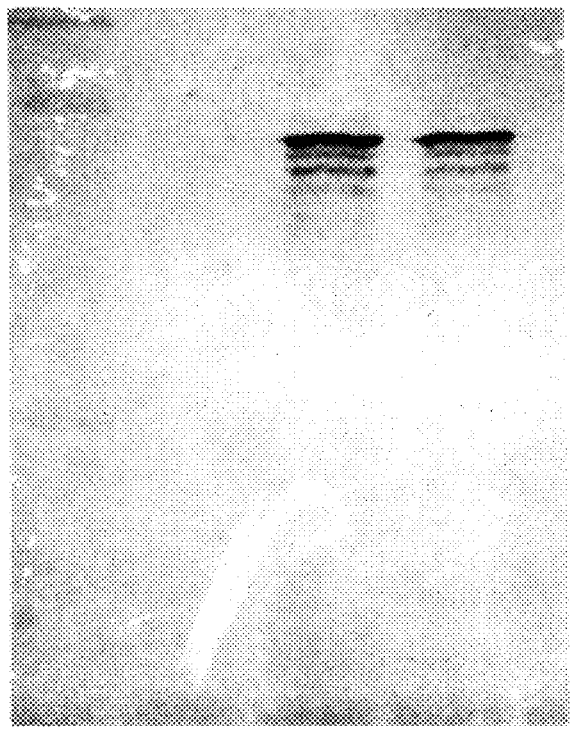
FIG. 1. Western blot analysis of *M. catarrhalis* proteins using as a probe monoclonal antibody 10F3, which recognizes the 80 kD OMP, later termed CopB. Lane A (m) is a Rainbow protein molecular weight marker (M.W. 14.3 to 200 kD, Amersham); Lane B (4B1) is a negative control comprising a whole cell lysate of 4B1/pBR322/RR1 (4B1 is an *M. catarrhalis* gene encoding an unrelated protein recognized by monoclonal antibody 4B1); Lanes C (3H8) and D (10F3) are whole cell lysates of 10F3/pBR322/RR1; and Lane E (B) is a blank control.

The present invention relates to the inventors' identification of particular outer membrane proteins (OMPs) of *Moraxella catarrhalis* that are found to have particularly useful properties, e.g., in the preparation of both diagnostic and therapeutic reagents. These proteins appear to be cell surface-exposed in their natural state, and exhibit molecular weights of about 30 kD, 80 kD and between about 200 and 700 kD, respectively, upon SDS-PAGE. Particular embodiments relate to the recombinant cloning of sequences encoding these proteins, antigenic subfragments, variants, and the like. The present invention also relates to monoclonal antibodies to these *M. catarrhalis* OMPs that are shown to reduce the number of infecting *M. catarrhalis* bacteria present in localized lung infections, as demonstrated in pulmonary clearance studies using a murine model system.

The OMP with a molecular weight of between about 200 and 700 kD, recognized by Mab 17C7, is often present in two forms, as assessed by SDS/PAGE and Western blotting. The larger, 200 to 700 kD, form barely enters the separating gel on SDS/PAGE. However, a smaller, ~100 kD, form of this antigen also exists and is often seen in Western blot analysis with Mab 17C7. This form may represent a breakdown product or subunit of the higher molecular weight form. Alternatively, the larger form of this antigen may be an aggregate of the smaller form. Whether the antigen preparation is heated at 100° C. or 37° C. prior to SDS-PAGE has also been found to affect the migration characteristics of the antigen(s) reactive with Mab 17C7 in Western blot analysis.

Recombinant clones;, expressing one or more of the selected OMPs, and that may be used to prepare purified OMP antigens as well as mutant or variant protein species in significant quantities, are included within the scope of the disclosure. The selected OMP antigen, and variants thereof, are anticipated to have significant utility in diagnosing and treating $M.$ $catarrhalis$ infections. For example, it is proposed that these OMP antigens, or peptide variants, may be used in immunoassays to detect $M.$ $catarrhalis$ or as a vaccine to treat $M.$ $catarrhalis$ infections.

To assist those of skill in carrying out more particular aspects of the invention, recombinant clones bearing DNA segments encoding, respectively, the 30 kD, 80 kD (CopB) and HMWP OMP antigens, were deposited with the American Type Culture Collection (ATCC) on Aug. 4, 1992, under the provisions of the Budapest Treaty. In particular, plasmid pMEH300 (ATCC accession number 69049) bearing a segment encoding the 30 kD OMP antigen; plasmid pMEH 120 (ATCC accession number 75285) bearing a segment encoding the 80 kD (CopB) OMP antigen; and phage MEH 200 (ATCC accession number 75286) bearing a segment encoding the HMWP antigen, were deposited in the form of either phage lysate (MEH 200), purified plasmid DNA (pMEH120) or recombinant $E.$ $coli,$ strain RR1 (pMEH300).

The pMEH300 plasmid can be characterized as a modified pLG338 vector in which pLG338 was digested with XhoI, and SacI linkers added. This new vector contains a $M.$ $catarrhalis$ chromosomal DNA insert of about 20 kb in size that can be excised by digestion with SacI. This insert contains an $M.$ $catarrhalis$ gene encoding the 30 kD antigen reactive with monoclonal antibody 8B6. The total vector size is therefore approximately 27 kb, with the vector comprising only about 7.3 kb.

Figure 8:
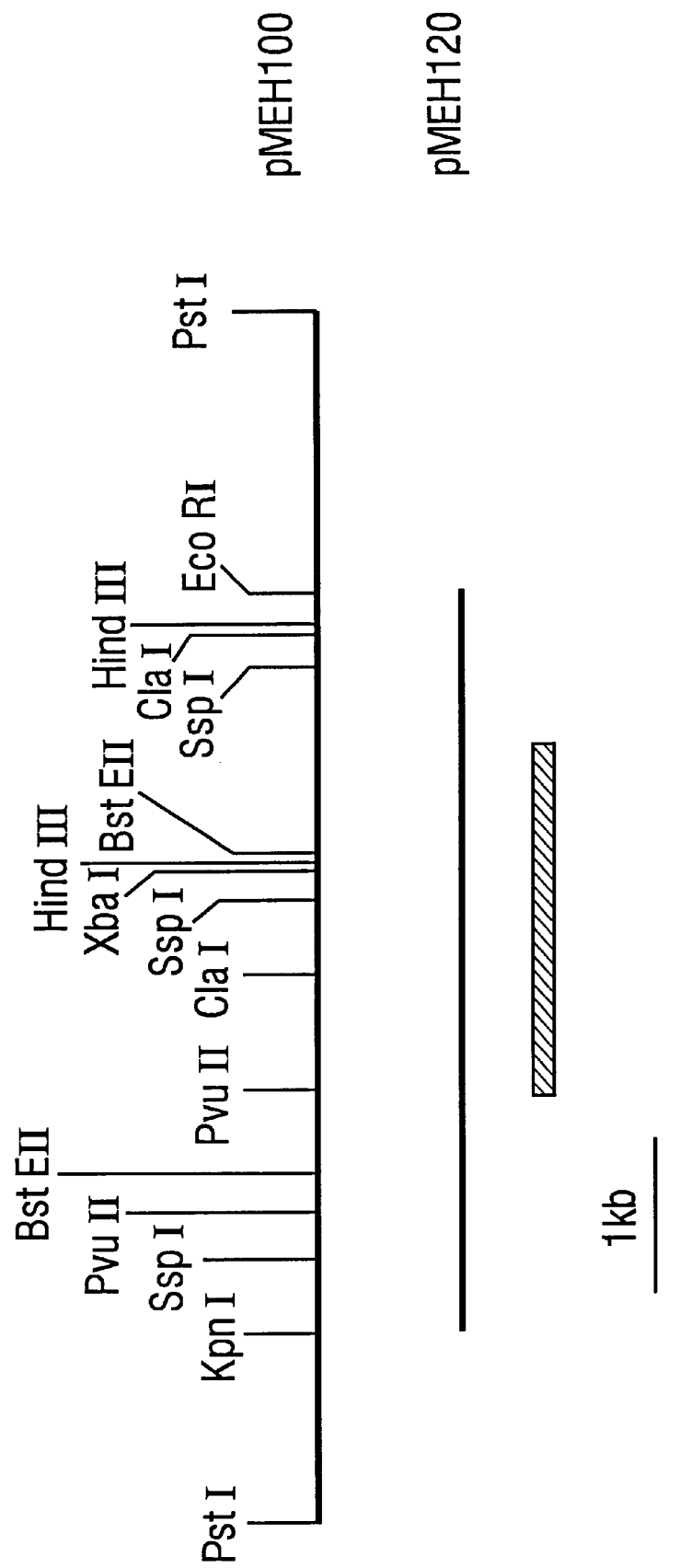
FIG. 8. Partial restriction enzyme map of the 7.8 kb *M. catarrhalis* DNA insert in the recombinant plasmid pMEH100. The thin bar immediately beneath the pMEH100 insert represents the 4.7 kb EcoRI-KpnI fragment subcloned from pMEH100 into pBluescript II for nucleotide sequence analysis; this subclone was designated as pMEH120. The thick shaded bar beneath the pMEH120 insert demarcates the extent of the copB gene.

The gene (copb) encoding the 80 kD OMP (CopB protein) was originally cloned in a pBR322-based recombinant plasmid, designated pMEH100. Subsequently, this gene was subcloned in pBluescript for sequencing analysis. This new plasmid, designated pMEH120, is what was deposited with the ATCC. Recombinant plasmid pMEH 120, is a pBluescript II SK+ vector containing an insert of $M.$ $catarrhalis$ chromosomal NA approximately 4.5 kb in size, and encodes a protein of about 80 kD that is reactive with monoclonal antibody 10F3. A preliminary restriction map of pMEH120 is set forth in FIG. 2, and a more complete map is shown in FIG. 8. The nucleotide and predicted amino acid sequence of the copB gene (seq id nos:1 and 2, respectively) are shown in FIG. 10.

Figure 3:
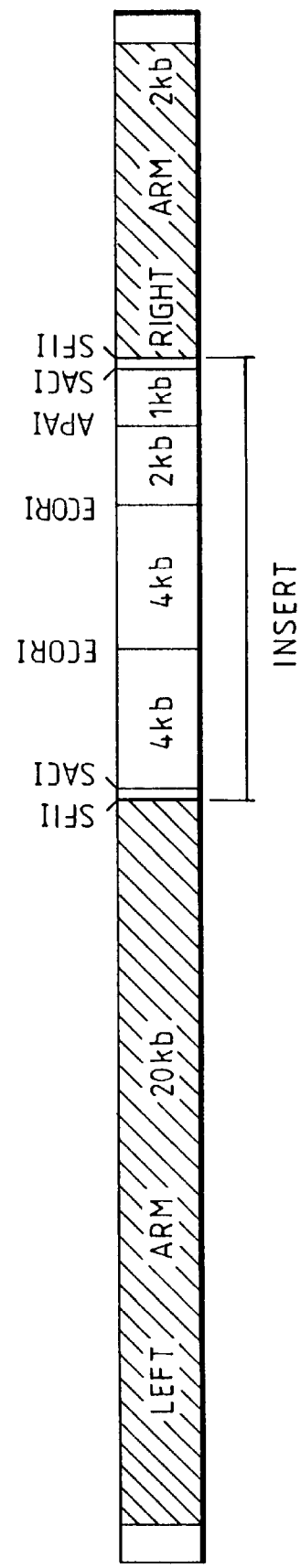
FIG. 3. Preliminary restriction map of phage MEH200, which comprises a segment encoding the Mab 17C7-reactive HMWP antigen.

The gene encoding the HMWP OMP antigen, reactive with Mab 17C7, was not subcloned out of the λGEM-11 phage used for the cloning work described in the examples below, phage MEH200. The λGEM-11 phage vector includes an $M.$ $catarrhalis$ chromosomal DNA insert of about 11 kb in size, which can be excised from the phage DNA by digestion with either SfiI or SacI. A preliminary restriction map is shown in FIG. 3.

As will be appreciated by those of skill in the art in light of the detailed disclosure set forth herein, that the invention is in no way intended to be limited by the foregoing or other specific embodiments that were deposited with the ATCC.

The nucleic acid sequences which encode for the selected OMP antigen, or their variants, may be useful in hybridization or polymerase chain reaction (PCR) methodology to detect $M.$ $catarrhalis.$ Accordingly, included in the present invention disclosure is information which may be used to prepare a wide variety of DNA fragments having a number of potential utilities, such as the preparation of relatively short immunogenic/antigenic peptidyl subfragments of the antigen, the use of DNA or RNA sequences in PCR and hybridization studies as probes for in vitro detection, as well as other useful medical and biomedical applications related to the research, diagnosis and treatment of $M.$ $catarrhalis$ infections.

The OMP antigens of the present invention are referred to, respectively, as the 30 kD, 80 kD and HMWP OMPs. The 80 kD OMP is also termed CopB and is the product of the copB gene. These proteins have been identified by the inventors by reference to monoclonal antibodies that were selected from a battery of monoclonal antibodies against $M.$ $catarrhalis$ outer membrane vesicles. These antibodies were employed as Western blot probes to identify corresponding antigens from SDS-PAGE runs of $M.$ $catarrhalis$ 035E outer membrane vesicle preparations. The monoclonal antibody recognizing the 30 kD OMP is termed 8B6, the antibody recognizing the 80 kD OMP (CopB) is termed 10F3, and that recognizing the HMWP kD antigen has been designated 17C7 (see FIGS. 1, 4 and 5). Importantly, each of the foregoing hybridomas have been shown to be protective against $M.$ $catarrhalis$ infection in animal models, and 17C7 is herein shown to effect enhanced pulmonary clearance of both homologous and heterologous $M.$ $catarrhalis$ strains.

As with the ATCC deposit of recombinant vectors and clones, hybridomas secreting the foregoing monoclonal antibodies that recognize the preferred OMP antigens have also been deposited with the ATCC under the provisions of the Budapest treaty on Jul. 30, 1992. The deposited hybridomas secrete, respectively, monoclonal antibody 8B6 (ATCC accession number HB11091), which recognizes the 30 kD OMP antigen; monoclonal antibody 10F3 (ATCC accession number HB11092), which recognizes the 80 kD (CopB) OMP antigen; and monoclonaL antibody 17C7 (ATCC accession number HB11093) which recognizes the HMWP OMP antigen.

The present invention envisions various means for both producing and isolating the OMP antigen proteins of the present invention, ranging from isolation of purified or partially purified protein from natural sources (e.g., from $M.$ $catarrhalis$ bacterial cells), or from recombinant DNA sources (e.g., $E.$ $coli$ or microbial cells). In the latter case, particularly for the CopB antigen, the OMP antigens, or antigenic peptides derived therefrom, may be provided in essentially antigenically pure states in that they will be free of other $M.$ $catarrhalis$ epitopes unrelated to the selected OMP species.

It is proposed that isolation of the OMP antigen from either natural or recombinant sources in accordance with the invention may be achieved isolating cell envelopes or outer membranes and then using a detergent-based purification scheme. In the case of recombinant cells, the desired antigen may be present in inclusion bodies.

Since monoclonal antibodies to the 30 kD, 80 kD (CopB) and HMWP OMP antigens are disclosed by the present invention, the use of immunoabsorbent techniques are anticipated to be useful in purifying the OMP antigen, or its immunologically cross reactive variants. It is proposed that useful antibodies for this purpose may be prepared generally by the techniques disclosed hereinbelow, or as in generally known in the art for the preparation of monoclonals (see, e.g., U.S. Pat. Nos. 4,514,498 and 4,740,467), and those reactive with the desired OMP protein or peptides selected. Moreover, it is believed that the foregoing general isolation scheme will work equally well for isolation of OMP variants or of antigenic/immunogenic subfragments of the protein, requiring only the generation and use of antibodies having affinity for the desired peptidyl region.

Additionally, by application of techniques such as DNA mutagenesis, the present invention allows the ready preparation of so-called "second generation" molecules having modified or simplified protein structures. Second generation proteins will typically share one or more properties in common with the full-length antigen, such as a particular antigenic/immunogenic epitopic core sequence. Epitopic sequences can be provided on relatively short molecules prepared from knowledge of the peptide, or underlying DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence.

Epitopic Core Sequences of the OMP Antigens

As noted above, it is proposed that particular advantages may be realized through the preparation of synthetic peptides which include epitopic/immunogenic core sequences. These epitopic core sequences are identified herein in particular aspects as hydrophilic regions of the OMP antigen. It is proposed that these regions represent those which are most likely to promote T-cell or B-cell stimulation, and, hence, elicit specific antibody production. An epitopic core sequence, as used herein, is a relatively short stretch of amino acids that is "complementary" to, and therefore will bind, antigen binding sites on OMP-directed antibodies. Additionally or alternatively, an epitopic core sequence is one that will elicit antibodies that are cross-reactive with OMP directed antibodies. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired OMP antigen with the corresponding OMP-directed antisera.

In general, the size of the polypeptide antigen is not believed to be particularly crucial, so long as it is at least large enough to carry the identified core sequence or sequences. The smallest useful core sequence anticipated by the present disclosure would be on the order of about 15 amino acids in length. Thus, this size will generally correspond to the smallest peptide antigens prepared in accordance with the invention. However, the size of the antigen may be larger where desired, so long as it contains a basic epitopic core sequence.

Accordingly, through the use of computerized peptide sequence analysis program (DNAStar Software, DNAStar, Inc., Madison, Wis.), the inventor proposes to identify particular hydrophilic peptidyl regions of the 30 kD, 80 kD (CopB) or HMWP OMP antigen which are believed to constitute epitopic core sequences comprising particular epitopes of the protein.

Syntheses of epitcpic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of 7.0 to 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptide(s) are stored in a lyophilized or powdered state, they may be stored virtually indefinitely, e.g., in metered aliquots that may be rehydrated with a predetermined amount of water (preferably distilled) or buffer prior to use.

Antigenically Functional Equivalent Amino Acids

As noted above, it is believed that numerous modifications and changes may be made in the structure of the desired OMP antigen, or antigenic/immunogenic subportions thereof, and still obtain a molecule having like or otherwise desirable characteristics.

It is known that certain amino acids may be substituted for other amino acids in a protein structure in order to modify or improve its antigenic or immunogenic activity (see, e.g., Kyte & Doolittle, 1982; Hopp, U.S. Pat. No. 4,554,101, incorporated herein by reference). For example, through the substitution of alternative amino acids, small conformational changes may be conferred upon an antigenic peptide which result in increase affinity between the antigen and the antibody binding regions. Alternatively, amino acid substitutions in certain OMP antigenic peptides may be utilized to provide residues which may then be linked to other molecules to provide peptide-molecule conjugates which retain enough antigenicity of the starting peptide to be useful for other purposes. For example, a selected OMP peptide bound to a solid support might be constructed which would have particular advantages in diagnostic embodiments.

The importance of the hydropathic index of amino acids in conferring interactive biologic function on a protein has been discussed generally by Kyte & Doolittle (1982), wherein it is found that certain amino acids may be substituted for other amino acids having a similar hydropathic index or core and still retain a similar biological activity. As displayed in Table I below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules. Preferred substitutions which result in an antigenically equivalent peptide or protein will generally involve amino acids having index scores within ±2 units of one another, and more preferably within ±1 unit, and even more preferably, within ±0.5 units.

TABLE I

| Amino Acid | Hydropathic Index |
| --- | --- |
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, will preferably be exchanged with an amino acid such as valine (+4.2) or leucine (+3.8). Alternatively, at the other end of the scale, lysine (−3.9) will preferably be substituted for arginine (−4.5), and so on.

Substitution of like amino acids may also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with an important biological property of the protein.

As detailed in U.S. Pat. No. 4,554,101, each amino acid has also been assigned a hydrophilicity value. These values are detailed below in Table II.

TABLE II

| Amino Acid | Hydrophilic Index |
| --- | --- |
| arginine | +3.0 |
| lysine | +3.0 |
| aspartate | +3.0 ± 1 |
| glutamate | +3.0 ± 1 |
| serine | +0.3 |
| asparagine | +0.2 |
| glutamine | +0.2 |
| glycine | 0 |
| threonine | −0.4 |
| alanine | −0.5 |
| histidine | −0.5 |
| proline | −0.5 ± 1 |
| cysteine | −1.0 |
| methionine | −1.3 |
| valine | −1.5 |
| leucine | −1.8 |
| isoleucine | −1.8 |
| tyrosine | −2.3 |
| phenylalanine | −2.5 |
| tryptophan | −3.4 |

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

Accordingly, these amino acid substitutions are generally based on the relative similarity of R-group substituents, for example, in terms of size, electrophilic character, charge, and the like. In general, preferred substitutions which take various of the foregoing characteristics into consideration will be known to those of skill in the art and include, for example, the following combinations: arginine and lysine; glutamate and aspartate; serine and threonine; glutamine and asparagine; and valine, leucine and isoleucine.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Preparation of Monoclonal Antibodies to *M. catarrhalis* OMPs

Monoclonal antibodies specific for the *Moraxella catarrhalis* OMPs of the present invention may be prepared using conventional immunization techniques. Initially, a composition containing antigenic epitopes of the OMP, such as an outer membrane vesicle preparation, can be used to immunize an experimental animal, such as a mouse, from which a population of spleen or lymph cells are subsequently obtained. The spleen or lymph cells can then be fused with cell lines, such as human or mouse myeloma strains, to produce antibody-secreting hybridomas. These hybridomas may be isolated to obtain individual clones which can then be screened for production of antibody to the desired OMP.

In particular aspects, the present invention utilizes outer membrane fragments from *M. catarrhalis* to induce an immune response in experimental animals. Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against outer membrane proteins. Hybridomas which produce monoclonal antibodies to the selected OMP are identified using standard techniques, such as ELISA and Western blot methods.

Hybridoma clones can then be cultured in liquid media and the culture supernatants purified to provide the OMP-specific monoclonal antibodies.

Use of Monoclonal Antibodies to OMP Antigens

In general, monoclonal antibodies to the desired OMP antigen of *M. catarrhalis* can be used in both the diagnosis and treatment of *M. catarrhalis* infections.

It is proposed that the monoclonal antibodies of the present invention will find useful application in standard immunochemical procedures, such as ELISA and Western blot methods, as well as other procedure which may utilize antibody specific to OMP epitopes. These OMP-specific monoclonal antibodies are anticipated to be useful various ways for the treatment of *M. catarrhalis* infections through, for example, their application in passive immunization procedures.

Additionally, it is proposed that monoclonal antibodies specific to the particular OMP may be utilized in other useful applications. For example, their use in immunoabsorbent protocols may be useful in purifying native or recombinant OMP species or variants thereof.

Studies have shown that antibody preparations against the OMP antigens of the invention have a significant protective effect against *M. catarrhalis* infection. The present inventors have shown that passive immunization with monoclonal antibodies specific for these OMPs significantly reduce the numbers of *M. catarrhalis* organisms following a bolus injection of bacteria. This demonstrates that these OMP antigens may be employed in making gammaglobulin preparations for use in passive immunization against disorders associated with *M. catarrhalis* infections, or used directly as vaccine components.

Recombinant Cloning Genes Encoding *M. catarrhalis* OMPs

To obtain suitable gammaglobulin preparations, one may desire to prepare monoclonal antibodies, preferably human or humanized hybridomas. Alternatively, it is proposed that one may desire to use globulin fractions from hyperimmunized individuals.

The present invention also involves isolating *M. catarrhalis* OMP genes, or sequence variants, incorporating DNA segments encoding the 30 kD, 80 kD (CopB) or HMWP OMP gene into a suitable vector, and transforming a suitable host, such that recombinant proteins, or variants thereof, are expressed. It will be appreciated by those of skill in the art that in light of the present disclosure the invention is also applicable to the isolation and use of the OMP gene sequences from any suitable source that includes appropriate coding sequences, such as any *M. catarrhalis* subspecies or isolate that expresses the desired OMP. Such sources may be readily identified by immunological screening with monoclonal antibodies to the selected OMP.

The preferred application of the present invention to the isolation and use of OMP-encoding DNA involves generally the steps of (1) isolation of Moraxella genomic DNA; (2) partial restriction enzyme digestion of the genomic DNA with an enzyme such as PstI, (the selected restriction enzyme is not crucial) to provide DNA having an average length of, e.g., 6 to 23 kb; (3) ligation of the partially digested DNA into a selected site within a selected vector, such as pBR322 (again, other plasmid or phage vectors may be used at this step, as desired); (4) transformation, transfection or electroporation of suitable host cells, e.g., *E. coli* cells, with the recombinant vector; and (5) selection of colonies expressing the desired OMP through the application of specifically designed screening protocols. Following identification of a clone which contains the OMP gene, one may desire to reengineer the gene into a preferred host/vector/promoter system for enhanced production of the outer membrane protein, or sequence variants thereof.

Through application of the foregoing general steps, the inventors have succeeded in identifying and selecting a number of clones which contain *M. catarrhalis* OMP genes in a manner which allows it to produce the corresponding outer membrane protein.

In a preferred application of these techniques, genomic DNA from *M. catarrhalis* strain 035E was isolated from bacteria through the use of SDS, ribonuclease and proteinase K treatment, phenol/chloroform/isoamyl alchohol extraction and ethanol precipitation. Conditions were determined for achieving an appropriate partial restriction enzyme digestion, such as would provide fragments on the order of 6–23 kb in length, using a restriction enzyme, such as PstI. After size fractionation, the partially digested Moraxella DNA fragments of the selected size range were ligated with fully digested vector, such as pBR322, which was fully digested with PstI to generate compatible sites for ligation with the genomic DNA fragments.

Following the ligation, the recombinant vectors are then used to transform a suitable host, such as *E. coli* RR1, to produce a recombinant library having members that express *M. catarrhalis* protein species encoded by the DNA fragment inserts. The recombinant microbial clones are cultivated, preferably on the surface of a nutrient agar, to form visible colonies. Those colonies expressing surface-exposed *M. catarrhalis* outer membrane proteins are then identified using monoclonal antibodies to *M. catarrhalis* OMPs in a colony blot radioimmunoassay. Recombinant *E. coli* clones expressing proteins having epitopes reactive with anti-OMP antibodies may then be cultured in desired quantities.

Host Cell Cultures and Vectors

In general, of course, prokaryotes are preferred for the initial cloning of DNA sequences and constructing the vectors useful in the invention. For example, *E. coli* strain RR1 is particularly useful. Other microbial strains which may be used include *E. coli* strains such as *E. coil* LE392, *E. coli* B, and *E. coil*×1776 (ATCC No. 31537). These examples are, of course, intended to be illustrative rather than limiting.

Prokaryotes are also preferred for expression. The aforementioned strains, as well as *E. coli* W3110 (F-, lambda-, prototrophic, ATCC No. 273325), bacilli such as *Bacillus subtilis*, or other enterobacteriaceae such as *Salmonella typhimurium* or *Serratia marcescens*, and various *Pseudomonas* species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as a transforming vector in connection with these hosts. For example, the phage lambda GEM™-11 may be utilized in making recombinant phage vector which can be used to transform host cells, such as *E. coli* LE392.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1980; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (EPO Appl. Publ. No. 0036776).

In addition to prokaryotes, eukaryotic microbes, such as yeast cultures may also be used. *Saccharomyces cerevisiae*, or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (*Tissue Culture,* 1973). Examples of such useful host cell lines are VEO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

As origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Sequencing of OMP Genes

After cloning the gene encoding the selected OMP, one will desire to perform restriction mapping and DNA sequence analysis, e.g., by the dideoxy method of Sanger et al. (1977). Both the DNA and the deduced amino acid sequence can then be compared with known sequences to determine homologies with known proteins. Sequencing has already been achieved for the 80 kD (CopB) OMP, as disclosed hereinbelow and presented in seq id nos:1 and 2. The amino acid sequence of the protein will reveal the nature of the various domains, e.g., cytoplasmic, membrane-spanning, and substrate binding domains, and give important information in terms of approaches to improving the structure of the enzyme through genetic engineering techniques.

Through the use of computerized peptide sequence analysis program (DNAStar Software, DNAStar, Inc., Madison, Wis.), particular hydrophilic peptidyl regions of the OMP antigen may be identified which are likely to constitute epitopic core sequences, comprising particular epitopes of the protein, as well as biologically functional equivalents of the foregoing peptides, as explained in more detail below.

Preparation of OMP Variants

Site-specific mutagenesis is a technique useful in the preparation of individual peptides, or biologically functional equivalent proteins or peptides, derived from the OMP antigen sequence, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art.

In general, site-d rected mutagenesis in accordance herewith is performed by first obtaining a single-stranded vector which includes within its sequence a DNA sequence which encodes the OMP antigen. An oligonucleotide primer bearing the desired mutated sequence is prepared, generally synthetically, for example by the method of Crea et al. (1978). This primer is then annealed with the single-stranded vector, and subjected to DNA polymerizing enzymes such as *E. coli* polymerase I Klenow fragment, in order to complete the synthesis cf the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected OMP gene using site-directed mutagenesis is provided as a means of producing potentially useful OMP species and is not meant to be limiting as there are other ways in which sequence variants of the OMP may be obtained. For example, recombinant vectors encoding the desired OMP gene may be treated with mutagenic agents to obtain sequence variants (see, e.g., a method described by Eichenlaub, 1979) for the mutagenesis of plasmid DNA using hydroxylamine.

The copB Gene and Protein

The present inventors have focused on the identification of cell surface-exposed antigenic components of *M. catarrhalis* that are both targets for antibodies that exhibit functional activity in biologically relevant systems and conserved among strains of this pathogen. One aspect of the present invention concerns the identification of a *M. catarrhalis* protein antigen termed CopB which is an outer membrane target for antibodies that enhanced the clearance of *M. catarrhalis* from the lungs of experimental animals.

Figure 11:
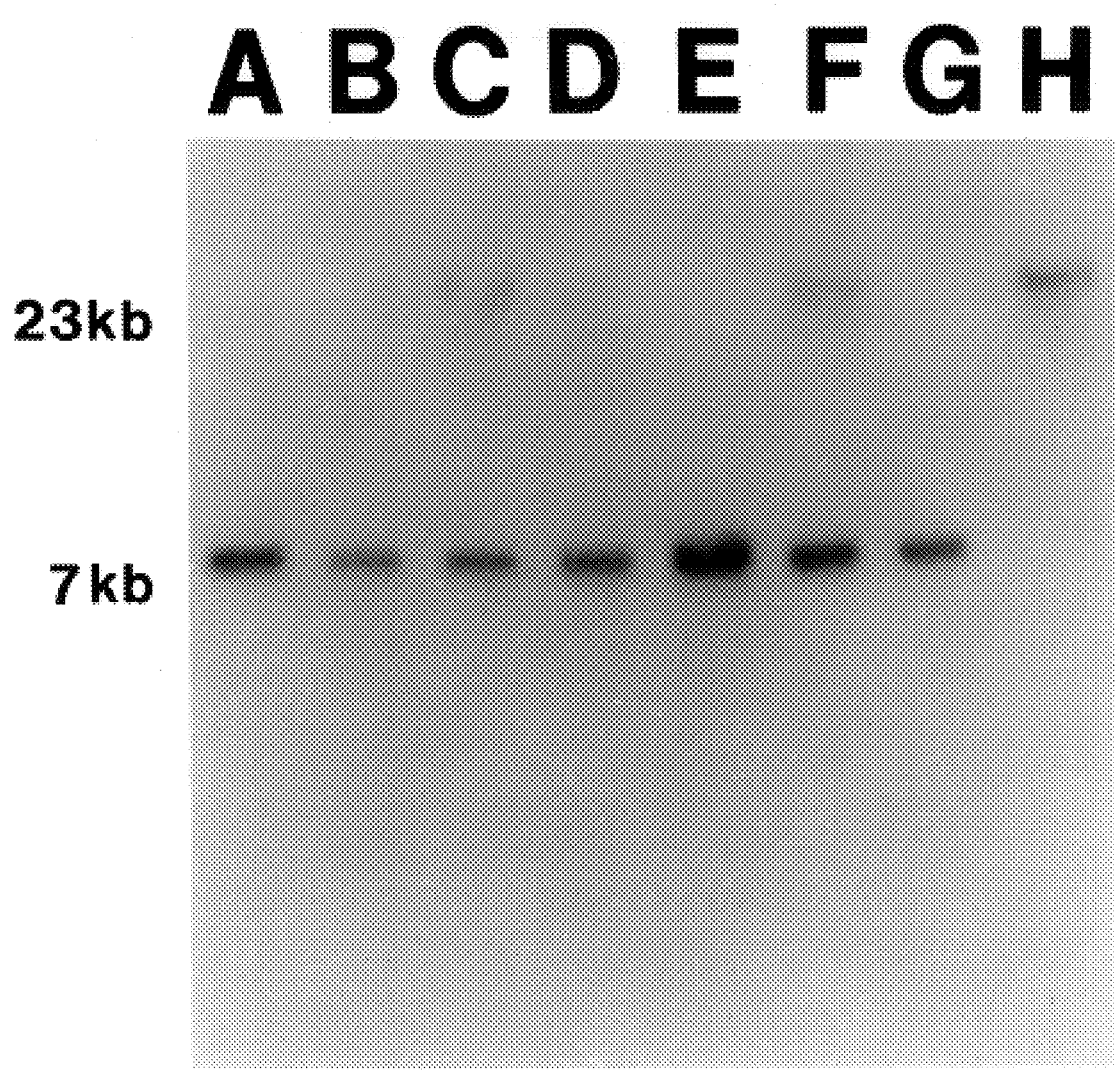
FIG. 11. Southern blot analysis of chromosomal DNA from eight *M. catarrhalis* strains using a copb-derived gene probe. Equivalent amounts of chromosomal DNA preparations from these eight strains were digested to completion with PstI and probed in Southern blot analysis using a 1.3 kb PvuII-XbaI fragment from the copb gene of strain 035E. Lane designations are identical to those in FIG. 3. Kb size markers are present on the left side of this figure.

The *M. catarrhalis* CopB outer membrane protein appears to be fairly well conserved among strains of *M. catarrhalis*, with the CopB-specific Mab 10F3 binding to the majority (70%) of 23 *M. catarrhalis* strains tested. This suggests that the relevant epitope is present in many, but not all, strains of this pathogen. Southern blot analysis using a probe consisting of an internal portion of the copB structural gene to probe chromosomal DNA from five Mab 10F3-reactive strains and three strains unreactive with this Mab showed that all eight strains' DNA hybridized with this probe (FIG. 11). This result suggests some degree of conservation of the copB gene at the nucleotide sequence level among these strains. Moreover, polyclonal antisera raised against outer membrane vesicles from two Mab 10F3-unreactive strains, TTA24 and B21, reacted with the recombinant CopB protein encoded by the copB gene derived from *M. catarrhalis* strain 035E, indicating some conservation of the protein structure of the CopB protein among the Mab 10F3-reactive (i.e., 035E) and Mab 10F3-unreactive (i.e., B21 and TTA24) strains.

The CopB protein is envisioned to be a promising candidate as a component for a *M. catarrhalis* vaccine. It is contemplated that the CopB protein will likely induce the synthesis of antibodies which enhance clearance of both homologous and heterologous strains of *M. catarrhalis* organism from the lungs of experimental animals, and hence will be suitable for inclusion into a vaccine to prevent respiratory tract disease caused by *M. catarrhalis*. The fact that the present invention makes the cloned copB gene available for the first time, will facilitate the production and purification of recombinant CopB protein for this purpose.

Use of Nucleic Acid Sequences

As mentioned, in certain aspects, the DNA sequence information provided by the present disclosure allows for the preparation of relatively short DNA (or RNA) sequences having the ability to specifically hybridize to gene sequences of the selected OMP antigen gere. In these aspects, nucleic acid probes of an appropriate length are prepared based on a consideration of the natural sequence or derived from flanking regions of the OMP gene, such as regions downstream of the gene as found in plasmid pBR322. The ability of such nucleic acid probes to specifically hybridize to OMP gene sequences lend them particular utility in a variety of embodiments. Most importantly, the probes can be used in a variety of diagnostic assays for detecting the presence of pathogenic organisms in a given sample. However, other uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 10 to 20, or so, nucleotide stretch of the sequence, although sequences of 30 to 50 or so nucleotides are also envisioned to be useful. A size of at least 10 nucleotides in length helps to ensure that the fragment will be of sufficient length tc form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. Thus, one will generally prefer to design nucleic acid molecules having OMP gene-complementary stretches of 15 to 20 nucleotides, or even longer, such as 30 to 50, where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

In that the OMP antigens of the present invention are believed to be indicative of pathogenic Moraxella species, the present invention will find particular utility as the basis for diagnostic hybridization assays for detecting OMP-specific RNA or DNA in clinical samples. Exemplary clinical samples that can be used in the diagnosis of infections are thus any samples which could possibly include Moraxella nucleic acid, including middle ear fluid, sputum, bronchoalveolar fluid, amniotic fluid or the like. A variety of hybridization techniques and systems are known which can be used in connection with the hybridization aspects of the invention, including diagnostic assays such as those described in Falkow et al., U.S. Pat. No. 4,358,535.

Accordingly, the nucleotide sequences of the invention are important for their ability to selectively form duplex molecules with complementary stretches of the corresponding OMP genes. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for soire applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15M–0.9M salt, at temperatures ranging from 20° C. to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, one may desire to employ nucleic acid probes to isolate variants from clone banks containing mutated clones. In particular embodiments, mutant clone colonies growing on solid media which contain variants of the OMP sequence could be identified on duplicate filters using hybridization conditions and methods, such as those used in colony blot assays, to only obtain hybridization between probes containing sequence variants and nucleic acid sequence variants contained in specific colonies. In this manner, small hybridization probes containing short variant sequences of the OMP gene may be utilized to identify those clones growing on solid media which contain sequence variants of the entire OMP gene. These clones can then be grown to obtain desired quantities of the variant OMP nucleic acid sequences or the corresponding OMP antigen.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, one will likely desire to employ an enzyme tag such as urease, alkaline phosphatase or peroxidase, instead of radioactive or other environmental undesirable reagents. In the case of enzyme tags, calorimetric indicator substrates are known which can be employed to provide a means visible to the human eye or spectrophoto-metrically, to identify specific hybridization with pathogen nucleic acid-containing samples.

In general, it is envisioned that the hybridization probes described herein will be useful both as reagents in solution hybridizations as well as in embodiments employing a solid phase. In embodiments involving a solid phase, the test DNA (or RNA) from suspected clinical samples, such as exudates, body fluids (e.g., amniotic fluid, middle ear effusion, bronchoalveolar lavage fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

In other embodiments, it is proposed that OMP sequences or variants thereof may be used to provide highly specific and sensitive detection of *M. catarrhalis* when used as reagents in polymerase chain reaction (PCR) assays. In general, by applying the PCR technology as set out, e.g., in U.S. Pat. No. 4,60,102, one may utilize various portions of the OMP sequence as oligonucleo-tide probes for the PCR amplification of a defined portion of OMP nucleic acid in a sample. The amplified portion of the OMP sequence may then be detected by hybridization with a hybridization probe containing a complementary sequence. In this manner, extremely small concentrations of *M. catarrhalis* nucleic acid may detected in a sample utilizing OMP sequences.

In other embodiments, OMP sequences may be utilized in PCR formats for the in vitro preparation of desired quantities of selected portions of the OMP gene. By amplifying selected gene portions of a selected OMP gene and then incorporating those portions into vectors, one can also prepare recombinant clones which express OMP variants, including subfragments of the OMP antigen. In this manner, peptides carrying antigen epitopes of the outer membrane protein may be prepared and utilized for various purposes.

Immunoassays

As noted, it is proposed that OMP peptides of the invention will find utility as immunogens, e.g., in connection with vaccine development, or as antigens in immunoassays for the detection of anti-OMP antigen-reactive antibodies. Turning first to immunoassays, in their most simple and direct sense, preferred immunoassays of the invention include the various types of enzyme linked immunosorbent assays (ELISAS) known to the art. However, it will be readily appreciated that the utility of OMP peptides is not limited to such assays, and that other useful embodiments include RIAs and other non-enzyme linked antibody binding assays or procedures.

In the preferred ELISA assay, peptides incorporating OMP antigen sequences are immobilized onto a selected surface, preferably a surface exhibiting a protein affinity such as the wells of a polystyrene microtiter plate. After washing to remove incompletely adsorbed material, one will desire to bind or coat a nonspecific protein such as bovine serum albumin (BSA) or casein onto the well that is known to be antigenically neutral with regard to the test antisera. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for from 2 to 4 hours, at temperahours, at temperatures preferably on the order of 25° to 27° C. Following incubation, the antisera-contacted surface is washed so as to remove non-immunccomplexed material. A preferred washing procedure includes washing with a solution such as PBS/Tween, or borate buffer.

Following formation of specific immunocomplexes between the test sample and the bound antigen, and subsequent washing, the occurrence and even amount of immunocomplex formation may be determined by subjecting same to a second antibody having specificity for the first. Of course, in that the test sample will typically be of human origin, the second antibody will preferably be an antibody having specificity in general for human IgG. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Active and Passive Immunization

The evaluation of the functional significance of antibodies to surface antigens of M. catarrhalis has been hampered by the lack of a suitable animal model. The relative lack of virulence of this organism for animals rendered identification of an appropriate model system difficult (Doern, 1986). Attempts to use rodents, including chinchillas, to study middle ear infections caused by M. catarrhalis were unsuccessful, likely because this organism cannot grow or survive in the middle ear of these hosts (Doyle, 1989). However, murine short-term pulmonary clearance models have now been developed (Unhanand et al., 1992; Verghese et al., 1990) which permit an evaluation of the interaction of M. catarrhalis with the lower respiratory tract as well as assessment of pathologic changes in the lungs. Using this model, it has been demonstrated that serum IgG antibody can enter the alveolar spaces in the absence of an inflammatory response and enhance pulmonary clearance of nontypable H. influenzae (McGehee et al., 1989), a pathogen with a host range and disease spectrum nearly identical to those of M. catarrhalis.

Results from studies using this model are presented herein which illustrate the success of various immunization regimens against M. catarrhalis. Passively immunization with monoclonal antibodies directed against the 30 kD, 80 kD (CopB) and HMWP OMPs is shown to enhance pulmonary clearance of homologous M. catarrhalis strains, as does passive immunization with antisera raised against M. catarrhalis outer membrane vesicles. Extending these findings, it was also determined that active immunization with outer membrane vesicles also results in the in vivo generation of antibodies which function to enhance pulmonary clearance of M. catarrhalis.

Importantly, results are also presented to demonstrate the success of protection against heterologous strains of M. catarrhalis. Firstly, passive immunization with the monoclonal antibody 17C7, raised against the HMWP OMP from M. catarrhalis strain 035E, was determined to confer protection against the heterologous strain TTA24. Secondly, passive immunization with polyclonal antisera raised against M. catarrhalis strain 035E outer membrane vesicles was also found to protect against pulmonary challenge with the heterologous M. catarrhalis strain TTA24.

The fact that active immunization with M. catarrhalis outer membrane vesicles resulted in enhanced clearance of this organism from the lungs after challenge indicates that immune factors can affect the interaction of this bacterium with the lower respiratory tract. Moreover, the positive effect of passive immunization with immune serum on pulmonary clearance indicates that serum antibodies likely play a major role in the observed immunoprotection. The protection observed against pulmonary challenge with a heterologous M. catarrhalis strain demonstrates that one or more conserved surface antigens are targets for antibodies which function to enhance clearance of M. catarrhalis from the lungs. It is contemplated that the relatively abundant and conserved 80 kD CopB antigen is one of these key antigens.

The results of this study mark a significant advance in the development of a vaccine against M. catarrhalis employing either purified outer membrane components alone, or outer membrane vesicles supplemented by additional components, for example, purified or recombinant OMPS such as the 80 kD CopB protein. To use M. catarrhalis outer membrane vesicles (OMVs) or outer membrane protein compositions as the basis for a human vaccine, the content of endotoxin (LPS) should be reduced, eliminated or de-toxified. The preparation of such compositions that are essentially free from endotoxin can be achieved by following published methodology. For example, U.S. Pat. No. 4,271,147 (incorporated herein by reference) discloses methods for the preparation of Neisseria meningitidis membrane proteins for use in vaccines; and Zollinger et al. (1978; 1979) describe the preparation of non-toxic protein and polysaccharide compositions essentially free from LPS.

Vaccine Preparation and Use

Immunogenic compositions, proposed to be suitable for use as a vaccine, may be prepared most readily directly from immunogenic OMP proteins and/or peptides prepared in a manner disclosed herein. Preferably the antigenic material is extensively dialyzed to remove undesired small molecular weight molecules and/or lyophilized for more ready formulation into a desired vehicle.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individuals immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as C. parvum or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

EXAMPLE I

Edta-Based Extraction of Outer Membrane Fragments

Various strains of M. catarrhalis may be obtained, for example, from research centers such as the Children's Medical Center (Dr. John Nelson) in Dallas, Tex. the University of Texas Health Science Center (Dr. Richard Wallace) in Tyler, Tex. the University of Michigan (Dr. Elliot Juni) in Ann Arbor, Mich. East Tennessee State University (Dr. Steven Berk) in Johnson City, Tenn. and the University of Massachusetts Medical Center (Dr. Gary Doern) in Worcester, Mass. Five well-studied strains have been described, including 035E, B21, TTA24, P48, and W1 (Unhanand et al., 1992). Strains 035E and TTA24 have been previously shown to be capable of persisting and growing in the lungs of normal mice (Unhanand et al., 1992). M. catarrhalis strains may be grown in Brain Heart Infusion (BHI) broth (Difco Laboratories, Detroit, Mich.) at 37° C. or at this same temperature on BHI agar plates in a 5% $CO_2$ atmosphere.

In order to obtain antibody to the OMP antigens, outer membrane fragments from M. catarrhalis strain 035E were prepared as an immunogen. M. catarrhalis strain 035E cells were grown in BHI broth. Plates were incubated at 37° C. in a candle extinction jar. Outer membrane fragments were subsequently prepared from these cells by the EDTA-based extraction procedure of Murphy & Loeb, (1989).

EXAMPLE II

Isolation and Characterization of M. catarrhalis Omps

In light of the present disclosure's identification of monoclonal antibodies specific to selected M. catarrhalis OMPs, it is proposed that the corresponding OMP antigen may be purified using the following general procedure. Cell envelopes will be prepared by sonication cr outer membrane fragments will be extracted by EDTA-based treatment of whole M. catarrhalis cells. These membranes will be treated with ionic or non-ionic detergents to release the desired proteins which can then be purified by using conventional column chromatography or by immunoaffinity techniques.

M. catarrhalis outer membrane vesicles may also be prepared from broth-grown cultures by the method of Murphy & Loeb (1989), and cell envelopes prepared from broth-grown cultures of M. catarrhalis as described by Hanson & Hansen (1991). Whole cell lysates of M. catarrhalis were prepared from BHI agar plate-grown cells (Patrick et al. 1987). SDS-PAGE and Western blot analysis were performed as described by Kimura et al. (1985); Kimura & Hansen (1986) and Patrick et al. (1987). Determination of whether a specific epitope was exposed on the bacterial cell surface and accessible to antibody was accomplished by means of the indirect antibody-accessibility assay (Kimura & Hansen, 1986).

The M. catarrhalis major outer membrane protein reactive with Mab 10F3 was purified from M. catarrhalis strain 035E by affinity chromatography using this Mab. Briefly, cell envelopes of strain 035E were solubilized in triple detergent (Kimura et al., 1985) and passed over a Protein A-Sepharose CL-4B column (Pharmacia, Piscataway, N.J.) over which Mab 10F3 had been passed previously in culture supernatant form. The outer membrane protein-antibody complex was eluted from the column with SDS-digestion buffer (Kimura et al., 1985) and dissociated by heating for 3 minutes at 100° C. in this buffer. The outer membrane protein was resolved by SDS-PAGE (Hunkapiller et al., 1983) and transferred to a polyvinylidene difluoride membrane by the method of Matsudaira (Matsudaira, 1987). N-terminal amino acid sequencing was performed on an amino acid sequencer (model 470A, Applied Biosystems, Foster City, Calif.) coupled to an on-line high-pressure liquid chromatography system (model 120A, Applied Biosystems).

EXAMPLE III

Preparation of Antidodies Specific for *M. catarrhalis* Outer Membrane Proteins A: Monoclonal Antibodies The present example illustrates the steps employed by the inventors in the generation and identification of hybridomas that produce monoclonal antibodies directed against the 30 kD, 80 kD (CopB) or HMWP OMP antigens. Once hybridomas secreting monoclonal antibodies to surface-exposed OMP antigens from *M. catarrhalis* were identified, those determined to produce antibody to these OMP antigens were selected and cultured to produce antibody for use in other studies, such as those involving pulmonary clearance of *M. catarrhalis*.

BALB/c mice were immunized by intraperitoneal injection with outer membrane fragments of *M. catarrhalis* strain 035E prepared by the EDTA-based extraction procedure. Each animal was immunized with 50–100 μg protein in 0.1 ml of Freund's complete adjuvant. One month later, the animals were boosted with an identical quantity of this same protein preparation in incomplete Freund's adjuvant. Three weeks later, the mice were given an intravenous injection (into the tail vein) with 50 μg protein of the same membrane preparation suspended in PBS.

The "pancake" fusion method was employed as follows: $SP_{2/0}$-Ag14 plasmacytoma cells were employed. These cells were maintained in DMEM (Dulbecco's Modified Eagle Medium)/Penicillin-Streptomycin-Glutamine with 15% fetal bovine serum, 1% Fungizone and 8-azaguanine. Two weeks prior to the fusion, some of the cells were split into media with 1% Fungizone but lacking 8-azaguanine. These cells were maintained for 10 days at a density of no greater than $1–2 \times 10^5$/ml. Beginning three days before the fusion, $SP_{2/0}$ cells were subcultured every 24 hours and maintained at an approximate density of $2–3 \times 10^5$/ml. Three days before the fusion, the mice were boosted intravenously with about 50 μg of protein immunogen. On the day of the fusion, two mice were sacrificed by cervical dislocation.

The spleens were removed aseptically and macerated. Spleen cells were collected in 10 mls of DMEM-HY media (60 ml NCTC-109, 6 tubes hypoxanthine-thymidine-glycine stock soln., 6 tubes oxaloacetic acid-bovine insulin stock soln., 12 ml penicillin-streptomycin-glutamine, 2.7 ml 100 mM Na pyruvate, and 508 ml DMEM). At room temperature, $SP_{2/0}$ cells and spleen cells were collected by centrifugation at 170×g for 11 min. in their respective tubes. $SP_{2/0}$ cells and spleen cells were each resuspended in a total of 5 mls of DMEM-HY media.

The hypoxanthine-thymidine-glycine stock solution was prepared by adding 136 mg hypoxanthine to 100 ml 0.1 M HCl, 38.7 mg thymidine to 100 ml $H_2O$, and 2.3 mg glycine to 20 ml $H_2$ O. These solutions were dissolved separately, combined and then aliquoted into 2.2 ml volumes.

The oxaloacetic acid-bovine insulin stock solution was prepared by dissolving 80.3 mg bovine insulin in 100 ml $H_2$ O, adding 1.32 gm oxaloacetic acid and aliquoting into 1 ml. volumes.

Spleen cells were then diluted to $2 \times 10^8$ cells/5 mls and the $SP_{2/O}$ cells was diluted to $2 \times 10^7$ cells/5 mls. The ratio of spleen cells to $SP_{2/O}$ cells was 10:1. Spleen cells were then mixed with $SP_{2/O}$ cells in a ratio of 1:1. The spleen-$SP_{2/O}$ mixture was then treated with 3 mls of 50% PEG/DMEM-HY media for 35 sec. Fused spleen-$SP_{2/O}$ cells were washed immediately with DMEM-HY and incubated in 30% HY:HIFCS (35 ml DMEM-HY, 15 ml FBS, filter) for 24 hours at 37° C. 24 hours after the fusion, media and fused cells were collected in 20% HY:HIFCS (80 ml DMEM-HY, 20 ml FBS, filter) by centrifugation at 170×g for 5 min. The fused cells were then resuspended in 100 mls of 20% HAT:HIFCS and transferred to 96-well microtiter plates, 100 μl/well. One week after the fusion, 100 μl of 20% HY:HIFCS were added to each well. Two weeks after the fusion, when wells containing proliferating hybrid cells became acidic, each positive well was split into a 2 ml well on a 24-well plate and the culture supernatant assayed for antibody characterization.

Supernatants from these clones were screened for antibodies to *M. catarrhalis* by ELISA binding and Western blot methods using EDTA-extracted outer membrane fragments of *M. catarrhalis* strain 035E as antigen for the ELISA, and whole cell lysates of this strain as antigen for Western blots. Positive supernatants were then tested by the indirect antibody accessibility RIA to investigate the surface exposure of outer membrane antigens as described by Kimura et al. (1985; 1986).

Positive hybridomas were then cultured in standard DME and the monoclonal antibodies were purified from culture supernatants on Protein A—Sepharose CL-4B as described by Ey et al. (1978.)

Each Mab identified as being reactive with *M. catarrhalis* in Western blot analysis was used in the indirect antibody accessibility assay to determine if these Mabs were reactive with surface-exposed determinants of this organism. The antibody accessibility assay performed was described by Patrick et al. (1987).

Nab 10F3, a murine IgG2a antibody, which reacted with an antigen with an apparent MW of approximately 80,000 in Western blot analysis, was shown to bind to the surface of whole cells of strain 035E. This Mab reacted with 4 of 10 different *M. catarrhalis* strains tested in colony blot-RIA analysis by the method of Gulig et al. (1987). This Mab was purified from hybridoma culture supernatant as described (Ey et al., 1978).

Mab 17C7 reacted with two different size bands in Western blot analysis. This Mab reacted with a band near the top of the gel that migrated in a diffuse form and sometimes with a second band that migrated with an apparent nW of between about 200 and about 700 kD. For the purpose of clarity, the Mab will be defined as being reactive with the "HMWP" antigen. This Mab bound to the surface of strain 035E and reacted with all ten different *M. catarrhalis* strains tested in the colony blot RIA.

Mab 8B6 reacted with an antigen with an apparent MW of approximately 30,000 in Western blot analysis. This Mab was also reactive with the surface of strain 035E and reacted with all ten different *M. catarrhalis* strains tested in the colony blot-RIA.

B: Polyclonal Antibodies

Polyclonal immune mouse sera were raised against outer membrane vesicles of *M. catarrhalis* strains B21 and TTA24. For each strain, three animals each received a primary immunization consisting of an intraperitoneal injection containing 50 μg (protein) of outer membrane vesicles suspended in complete Freund's adjuvant (Difco Laboratories). Four weeks later, these animals received an intraperitoneal injection with 50 μg (protein) of the homologous outer membrane vesicles suspended in pH 7.3 phosphate-buffered saline. Blood was drawn for serum preparation two weeks later.

EXAMPLE IV

Cloning the copB Gene Encoding the 10F3-Reactive 80 kD Omp (CopB) from *M. catarrhalis*

The present example illustrates steps employed by the inventors in cloning the gene encoding the 80 kD (CopB)

OMP from *M. catarrhalis*. This example discloses one or more preferred recombinant *E. coli* clones, expressing the 80 kD (CopB) OMP antigen, isolated by the following procedures.

A. Isolation of Genomic DNA

*M. catarrhalis* strain 035E was used as a representative Moraxella pathogen in this study. Genomic DNA from *M. catarrhalis* strain 035E was extracted and purified as follows. *M. catarrhalis* cells (approximately 2 gms wet weight) were scraped from agar plates and resuspended in 20 mls. PBS. To this suspension was added 3.2 ml 10% (w/v) SDS and 1 ml RNase (10 mg/ml). This mixture was incubated at 37° C., then 3 mg proteinase K added, followed by further incubation at 55° C. overnight. The incubated mixture was then extracted once with phenol, twice with phenol:chloroform:isoamyl alcohol, and three times with chloroform:isoamyl alcohol. The resulting DNA was then precipitated with two volumes of absolute ethanol, and collected with a Pasteur pipet.

B. Preparation of an *M. catarrhalis* genomic library in pBR322

The partial digestion of genomic DNA was achieved by incubating 100 µg portions of *M. catarrhalis* genomic DNA with varying amounts of the restriction enzyme PstI in a reaction volume of about 1.5 ml. at 37° C. for 1 hr. The partially digested genomic DNA was then size fractionated by sucrose density gradient centrifugation. Fractions containing DNA fragments from about 6 kb to 23 kb in length, and preferably from about 6 kb to about 15 kb in length, were selected and dialyzed to obtain purified genomic DNA fragments for ligation with pBR322.

The plasmid vector pBR322 was fully digested with PstI by incubating 15 µg portions of pBR322 with 50 units of PstI in a 100 µl reaction volume at 37° C. for 18 hrs. Ligation of the purified DNA fragments into the PstI-digested pBR322 vector was accomplished by incubating 300 ng of the purified DNA fragments and PstI-digested pBR322 together with ATP and T4 DNA ligase under conditions described by Sambrook et al. (1989). After ligation, the DNA was diluted 1:5 with 10 mM TRis-HCl (pH 8.0) and was used to transform *E. coli* RR1 made competent by the CaCl$_2$ method.

C. Screening Transformed RR1 Colonies by Colony Blot-Radioimmunoassay for *M. catarrhalis* OMP Expression A colony blot RIA was then carried out as described by Gulig et al. (1987) with monoclonal antibody 10F3 as the primary antibody.

D. Characterizing Recombinant *E. coli* Clones Expressing *M. catarrhalis* OMP Antigens Clones which reacted with monoclonal antibody 10F3 in the colony blot RIA were cultured using LB medium containing the antibiotic tetracycline (15 µg/ml). Whole cell lysates of recombinant *E. coli* RR1 expressing *M. catarrhalis* OMP antigens were prepared as described by Patrick et al. (1987). Briefly, portions of these whole-cell lysates were subjected to SDS-PAGE as described in Gulig et al. (1987) and then stained with Coomassie blue or transferred to nitrocellulose for Western blot analysis.

Figure 2:
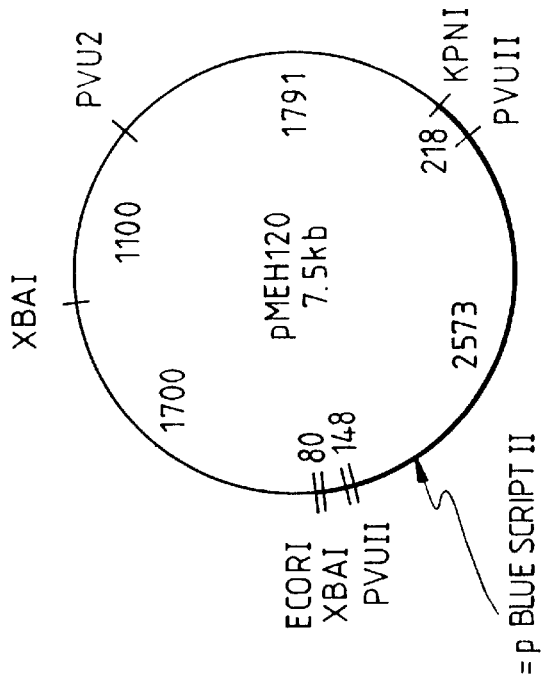
FIG. 2. Preliminary restriction map of pMEH120, which comprises a segment encoding the Mab 10F3-reactive 80 kD antigen, later termed CopB.

The results shown in FIG. 1 indicate that a recombinant 80 kD OMP gene (copB) was expressed in clones identified by monoclonal antibody 10F3. Restriction enzyme analysis of the recombinant plasmid in this clone, designated pMEH100, revealed the presence of a 7.8 kb *M. catarrhalis* DNA insert. For sequence analysis, a 4.7 kb subfragment of pMEH100 was subcloned in a pBluescript SK+ vector (pMEH120). A preliminary restriction analysis of pMEH120 is shown in FIG. 2. Further characterization of this recombinant clone is described hereinbelow in Example VII.

EXAMPLE V

Cloning of the Genes Encoding the 30 kD (8B6-Reactive) and 100 kD (17C7-Reactive) Outer Membrane Proteins of *M. catarrhalis*

A. Isolation of Genomic DNA

In other cloning procedures, *M. catarrhalis* genomic DNA was isolated and purified from strain 035E, and 100 µg samples were partially digested with Sau3A (Promega Biotech) at room temperature, as described above for PstI.

B. Preparation of a *M. catarrhalis* Genomic DNA Library Using the Bacteriophage Vector λGEM-11

The digested DNA was size-fractionated in sucrose density gradients and fragments of DNA 15 kb and larger were collected for use in library construction. These DNA fragments (1 µg) were filled in using the Klenow procedure (Promega) at 14° C. for 90 minutes. These fragments were then cleaned by standard procedures and ligated onto the phage DNA arms and packaged using the protocol and reagents supplied by Promega in the LambdaGEM-11 * Xho I Half-Site Arms Cloning System, except that T4 DNA ligase from BRL was used. After packaging, the phage-based library was titered using *E. coli* LE392. This genomic library contained 50,000 recombinant clones.

C. Screening of the Bacteriophage-Based Genomic DNA Library with Monoclonal Antibodies 17C7 and 8B6

To screen the clone bank, 20,000 plaques were immunoreacted with Mabs 17C7 and 8B6 using the plaque screening procedure described in Current Protocols in Molecular Biology (Wiley Interscience) using rad:ioiodinated goat anti-mouse Ig as the probe to detect Mabs bound to plaque material. One recombinant phage reactive with each Mab was ultimately identified.

D. Characterization of the Recombinant Phages Reactive with Mabs 17C7 and 8B6

Liquid lysate cultures of these recombinant phage were prepared by the standard methods described in Current Protocols in Molecular Biology. The DNA was extracted using standard methods. Phage harvested from liquid lysates were heated at 100° C. for 3 min. in standard SDS digestion buffer and then used for SDS-PAGE and Western blot analysis to confirm that these recombinant phage were expressing the appropriate *M. catarrhalis* antigens.

The recombinant phage reactive with Mab 17C7, designated MEH200, were found to comprise DNA coding for the HMWP. A preliminary restriction map of MEH200 is shown in FIG. 3 to comprise an insert of about 11 kb in size. A second clone, designated pMEH3000, was found to incorporate a DNA segment of about 18 kb in size, encoding for the Mab 8B6-reactive 30 kD antigen.

Figure 4:
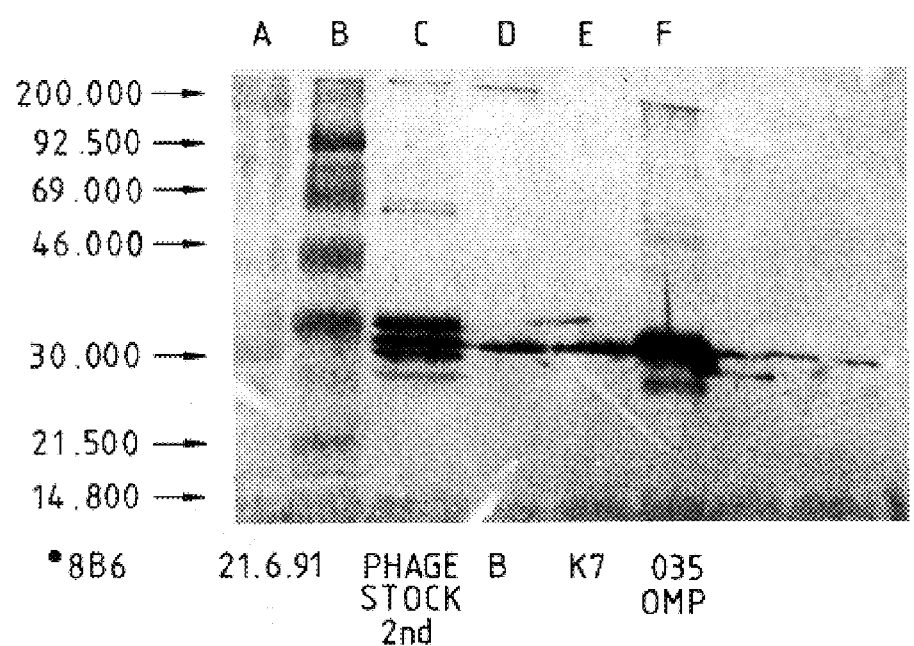
FIG. 4. Western blot analysis of *M. catarrhalis* proteins using as a probe monoclonal antibody 8B6, which recognizes the 30 kD OMP. Lane A is a. Rainbow protein molecular weight marker (M.W. 14.3 to 200 kD, Amersham); Lane B is a prestained SDS-PAGE-standard, low molecular weight (M.W. 16 to 110 kD, Bio-Rad); Lane C contains proteins from a phage lysate of recombinant *E. coli* that express the 30 kD OMP (LE392/8B6); Lane D is a blank control; Lane E is a negative control (phage lysate from recombinant *E. coli* expressing the HMWP OMP, LE392/17C7); and Lane F is a positive control (*M. catarrhalis* 035E outer membrane vesicles).

FIG. 4 is an illustrative Western blot analysis of proteins from *E. coli* clone LE392/8B6, which expresses the 30 kD OMP antigen. In this study, the various indicated samples were subjected to PAGE, transferred to a nitrocellulose membrane, and probed with the 30 kD OMP-specific monoclonal antibody 8B6. As can be seen, a band having an approximate molecular weight of 30 kD is seen in the LE 392/8B6 lane (lane C), and a similar band is seen in the position control lane (lane F). The nature of the two additional bands seen in the LE 392/8B6 lane (lane C) is unclear, but they could be due to processing of the recombinant protein or overloading of the gel. The bands seen in the negative control lanes (lanes D and E) are clearly due to spillover from lanes C and F.

FIG. 5 shows a similar Western blot analysis of a phage lysate from a clone expressing the HMWP OMP, designated LE 392/17C7, probed with monoclonal antibody 17C7. Lanes C–E comprise phage lysate proteins from clone LE392/17C7. These lanes each exhibit a strongly reactive in the very high molecular weight range.

EXAMPLE VI

Conservation of the *M. catarrhalis* 80 kD Protein (CopB) Between Strains

The present example illustrates the further characterization of the 80 kD *M. catarrhalis* OMP termed CopB, including an analysis of this protein in 23 different strains of *M. catarrhalis*.

Figure 6:
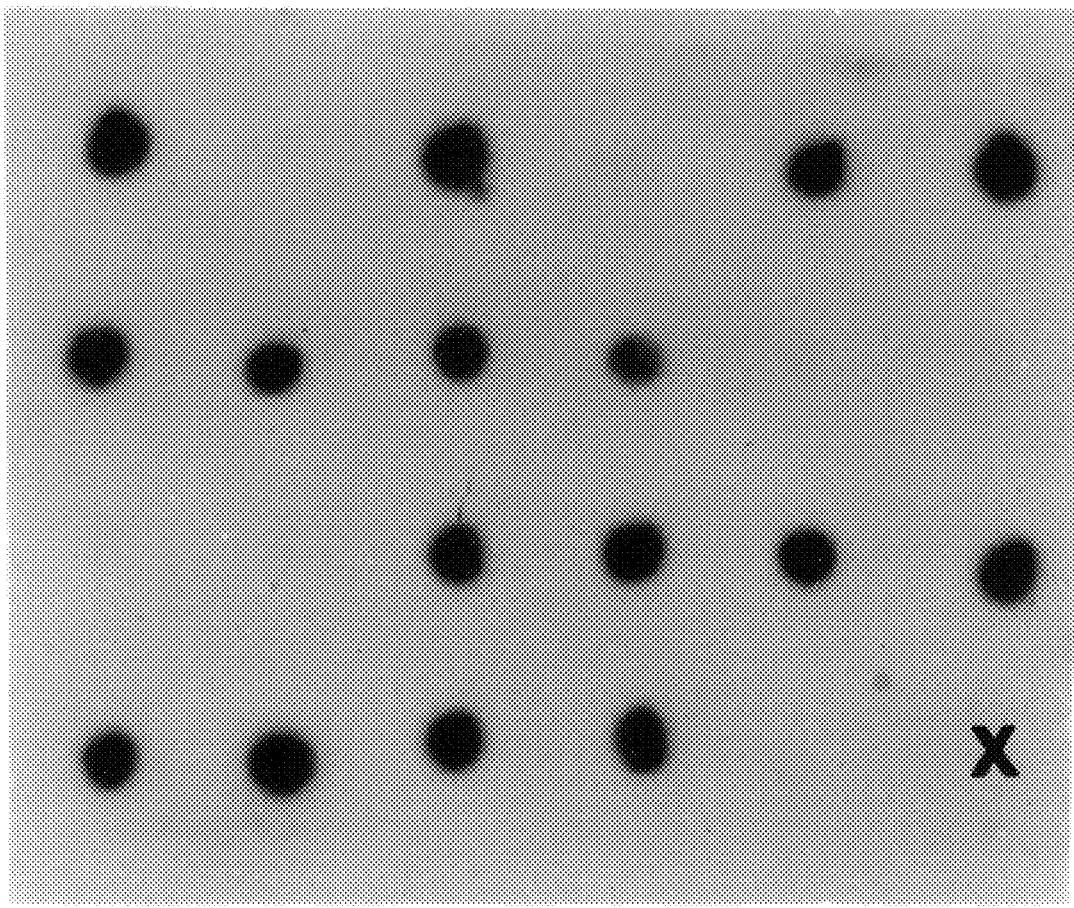
FIG. 6. Autoradiograph depicting the reactivity of Mab 10F3 with 23 *M. catarrhalis* strains in the colony blot-radiommunoassay. These 23 strains and *E. coli* RR1 (a negative control) were arranged in a 4×6 grid pattern on the filter paper; the x marks the position of the *E. coli* cells. After incubation with Mab 10F3, the filter was probed with radioiodinated goat anti-mouse immunoglobulin and processed for autoradiography (Gulig et al., 1983).

In preliminary Western blot studies, Mab 10F3 was found to be directed against an outer membrane protein of *M. catarrhalis* strain 035E which exhibited an apparent molecular weight of approximately 80,000 on SDS/PAGE. Use of Mab 10F3 in the indirect antibody-accessibility assay revealed that it bound to the surface of *M. catarrhalis* strain 035E (Table III), indicating that this Mab reacted with a surface-exposed epitope of the 80kDa outer membrane protein in this strain. When 23 strains of *M. catarrhalis* were probed with this same Mab in colony blot-radioimmunoassay analysis, 16 (70%) of these strains bound this Mab (FIG. 6).

TABLE III

ANTIBODY ACCESSIBILITY OF THE PROTEIN EPITOPE DEFINED BY ITS REACTIVITY WITH MAB 10F3

| Bacterial Strain | Binding[a] pf Mab | |
|---|---|---|
| | 10F3[b] | 2F4[c] |
| *M. catarrhalis* strain 035E | 121,888 | 5,022 |
| *E. coli* HB101 (pBR322) | 1,122 | 788 |
| *E. coli* HB101 (pMEH100) | 136,462 | 938 |

[a]Counts per minute of $^{125}$I-labeled goat anti-mouse immunoglobulin bound to Mabs attached to the bacterial cell surface as determined in the indirect antibody-accessibility assay.
[b]Mab 10F3 is a murine IgG antibody specific for an epitope on the *M. catarrhalis* outer membrane protein with an apparent molecular weight of 80 kDa in SDS-PAGE.
[c]Mab 2F4 is a murine IgG antibody specific for a *Haemophilus influenzae* type b outer membrane protein (Gulig et al., 1990); it is included here as a negative control.

Based on the results described above, eight of these 23 strains were selected for further analysis by SDS-PAGE and Western blotting. These representative strains included five (i.e., 035E, P44, TTA1, TTA37, and W1) reactive with Mab 10F3 in the colony blot-radioimmunoassay and three strains (i.e., B21, P48, and TTA24) that were unreactive with this Mab. When outer membrane vesicles of these eight strains were resolved by SDS-PAGE and stained with Coomassie blue, it was apparent that six of these strains (FIG. 7, panel 1, lanes A and C through G) possessed a major outer membrane protein that migrated at a rate similar or identical to that of the 80 kDa major outer membrane protein in strain 035E (FIG. 7, panel 1, lane B). The eighth strain (W1) had only a minor protein band that migrated at this rate (FIG. 7, panel 1, lane H). Western blot analysis using Mab 10F3 confirmed that the five strains reactive with this Mab in the colony blot-radioimmunoassay each possessed an antigen band that migrated in SDS-PAGE at about the same rate (FIG. 7, panel 2, lanes B, C, E, G, and H). The single strain (W1) that did not have a major outer membrane protein with an approximate molecular weight of 80 kD did exhibit a Mab 10F3-reactive antigen band that migrated at about the same rate (FIG. 7, panel 2, lane H) as did the other Mab 10F3-reactive proteins.

The presence of the 80 kD protein in all of the *M. catarrhalis* strains analyzed by SDS-PAGE or Western blot analyses (FIG. 7), and its relative abundance in the outer membrane in the majority of the strains examined in this study, attests to the importance of this protein. *Branhamella* (*Moraxella*) *catarrhalis* OMPs have previously been grouped into classes, OMP-A to OMP-H, according to the apparent molecular weight of protein bands on SDS/PAGE (Murphy & Loeb, 1989; Murphy, 1989). In that the presently-cloned protein migrates with an apparent molecular weight of 80 kD protein in this system, it has been designated as *Moraxella catarrhalis* outer membrane protein B (CopB). It is important to note that only with the purification and, preferably, with the molecular cloning of OMPs, can the proteins be definitively characterized and identified and the problems associated with SDS gel designations, such as the lack of purity, and particularly, the presence of several bands with similar molecular weights, be overcome.

EXAMPLE VII

Sequencing and characterization of the *M. catarrhalis* copB Gene and Protein The present example illustrates steps employed by the inventors in further characterizing and sequencing the copB gene which encodes the 80 kD *M. catarrhalis* CopB protein antigen.

Preparation of plasmid DNA by the mini-prep method, purification of DNA fragments by agarose gel electrophoresis, and Southern blot analysis of *M. catarrhalis* chromosomal DNA preparations were performed as described by Sambrook et al. (Sambrook et al., 1989). Nucleotide sequence analysis of a 4.7 kb EcoRI-KpnI *M. catarrhalis* DNA fragment (bearing the gene encoding the outer membrane protein reactive with Mab 10F3) contained in pBluescript II (Stratagene Cloning Systems, La Jolla, Calif.) was performed using nested deletions and other standard methods. The nucleotide sequence information was analyzed by using the Intelligenetics Suite package and programs from the University of Wisconsin Genetics Computer Group sequence analysis software package (Devereux et al., 1984).

Figure 9:
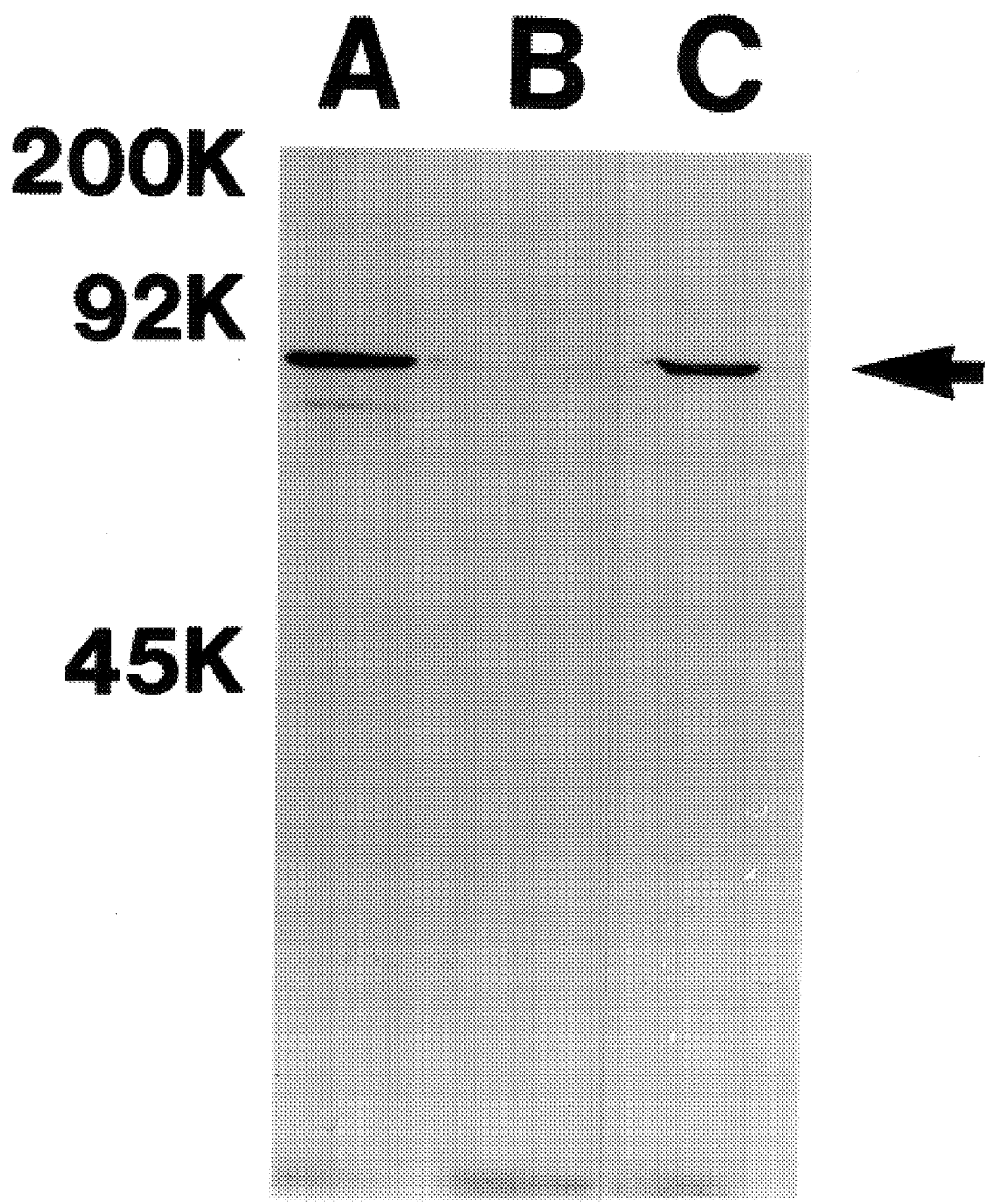
FIG. 9. Western blot analysis of the reactivity of Mab 10F3 with *M. catarrhalis* and recombinant *E. coli* strains. Proteins present in cell envelopes of *M. catarrhalis* strain 035E (lane A) and in whole cell lysates of *E. coli* RR1 (pBR322) (lane B) and of the recombinant strain *E. coli* RR1(pMEH100) (lane C) were resolved by SDS-PAGE, transferred to nitrocellulose, and probed with Mab 10F3 in Western blot analysis. The arrow indicates the position of the CopB protein. Molecular weight position markers are present on the left side of this figure.

Restriction enzyme analysis of the recombinant plasmid, designated pMEH100, in the clone identified by the Mab 10F3 revealed the presence of a 7.8 kb *M. catarrhalis* DNA insert (FIG. 8). Western blot analysis of the proteins expressed by the recombinant strain *E. coli* RR1(pMEH100) indicated that this strain expressed a Mab 10F3-reactive antigen that migrated at a rate indistinguishable from that of the native CopB protein of *M. catarrhalis* strain 035E (FIG. 9, lanes A and C). Further characterization of this recombinant clone using the indirect antibody-accessibility assay revealed that, when the *M. catarrhalis* CopB protein was expressed in a recombinant *E. coli* strain, this protein was translocated to the cell surface where it bound Mab 10F3 (Table III).

Subcloning experiments localized the region of the *M. catarrhalis* DNA insert in pMEH100 encoding the CopB protein to a 4.7 kb EcoRI-KpnI fragment. This fragment was subcloned into the plasmid vector pBluescript II for nucleotide sequence analysis; the resultant recombinant plasmid was designated pMEH120. Both strands of this latter DNA insert were sequenced in their entirety.

An open reading frame containing 2,276 bp was identified in this *M. catarrhalis* insert, the primary translation product of which was calculated to have a molecular weight of 83,040. The nucleotide sequence of this gene, designated copB, is depicted in FIG. 10 (seq id no:1). The open reading frame begins at position 100 and ends at position 2,376. A hexanucleotide sequence (5'-TTGACA-3') beginning at position 55 has similarity to the -35 promoter consensus sequence, but no appropriately positioned -10 consensus sequence could be identified. No inverted nucleotide repeats were found 3' from the termination codon (TAA at position 2,377), and no additional open reading frames were identified downstream in the remaining nucleotide sequence. A search of relevant data bases, including EMBL, GenBank, PIR, and Swiss-Prot, with both the nucleotide sequence and translation product of the copB gene did not yield any genes or gene products with significant similarity.

Examination of the predicted amino acid sequence (seq id no:2) of the translaticn product of the copB gene revealed a possible leader peptide, encoded by bases 100–168 (FIG. 10), with a signal peptidase I consensus sequence cleavage site (i.e., Ala-X-Ala) at the expec:ed position (Nikaido & Vaara, 1985; FIG. 10). This was confirmed by obtaining the N-terminal amino acid sequence of the CopB protein purified by affinity chromatography from *M. catarrhalis* strain 035E; there was 100% identity between this N-terminal sequence consisting of 21 amino acids and the deduced amino acid sequence after the proposed cleavage site. The calculated molecular weight of the mature CopB protein was 80,601.

Chromosomal DNA was purified from both strain 035E and seven other *M. catarrhalis* strains for use in Southern blot analysis. These eight strains included five that were reactive with Mab 10F3 in Western blot analysis and three strains which lacked reactivity with this Mab. These DNA preparations were digested with PstI and probed in Southern blot analysis with a 1.3 kb PvuII-XbaI fragment containing approximately 66% of the copB structural gene from strain 035E. All eight strains, regardless of their reactivity with Mab 10F3 in Western blot analysis, were found to possess DNA fragments reactive with this gene probe (FIG. 11). Interestingly, seven of the eight strains yielded a 7–8 kb PstI fragment that hybridized this probe (FIG. 11, lanes A–G). A single strain (W1) which was reactive with Mab 10F3 in Western blot analysis exhibited a much larger fragment that hybridized with the copB probe (FIG. 11, lane H). Repeated experiments confirmed this latter result, making strain W1 the only one of the eight studied that did not possess a 7–8 kb PstI fragment that hybridized this copb probe.

EXAMPLE VIII

Antigenic Cross-Reactivity of CopB Proteins Among *M. catarrhalis* Strains

This example relates to an analysis of the antigenic cross reactivity of the CopB proteins among different *M. catarrhalis* strains.

The results from the Southern blot analyses described above suggested that the genes encoding CopB proteins were fairly well conserved among different strains of *M. catarrhalis* (FIG. 11). However, the fact that three of the eight strains described above did not express a CopB protein reactive with Mab 10F3 indicated the existence of some degree of antigenic heterogeneity of the CopB protein among these strains. To determine whether the CopB proteins of the Mab 10F3-unreactive strains possessed any antigenic determinants common to the CopB protein of strain 035E, mice were immunized with outer membrane vesicles from *M. catarrhalis* strains B21 and TTA24 to prepare polyclonal antisera reactive with the CopB proteins of these two strains.

Figure 12A:
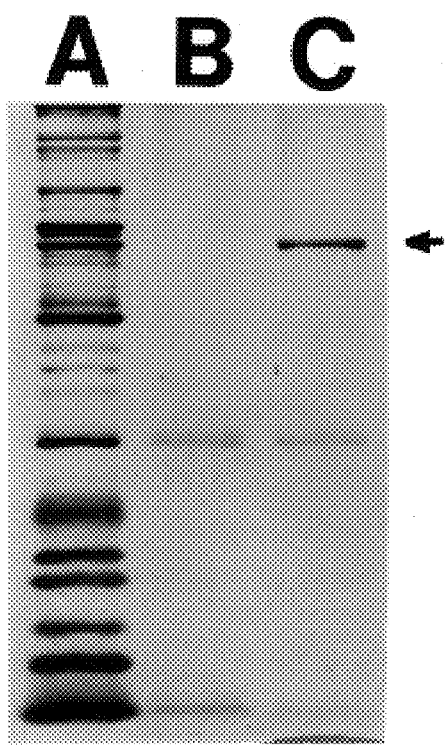
FIG. 12. Western blot analysis of the reactivity of the recombinant CopB protein encoded by the copb gene from *M. catarrhalis* strain 035E with polyclonal mouse antisera raised against outer membrane vesicles of *M. catarrhais* strains B21 and TTA24. Proteins present in outer membrane vesicles from the homologous *M. catarrhalis* strain (B21 in lane A and TTA24 in lane D), in cell envelopes from *E. coli* RR1(pBR322) (lanes B and E), and in cell envelopes from the recombinant strain *E. coli* RR1(pMEH100) (lanes C and F) were resolved by SDS-PAGE, transferred to nitrocellulose, and probed with mouse antiserum to outer membrane vesicles of either strain B21 (panel 1) or strain TTA24 (panel 2). The arrows indicates the position of the CopB protein.
Figure 12B:
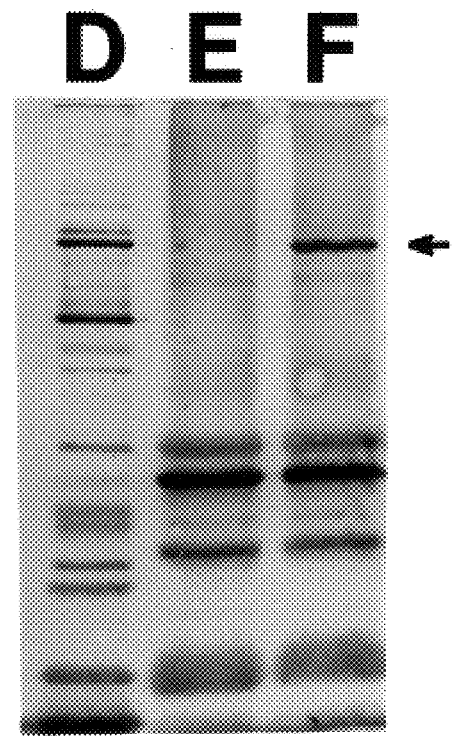

The B21 and TTA24 antisera were used in Western blot analyses to probe the recombinant CopB protein from strain 035E as expressed in *E. coli*. Both of these two different polyclonal antisera reacted with this recombinant protein from strain 035E (FIG. 12, panel 1, lane C, and panel 2, lane F), indicating that the CopB proteins of strains B21 and TTA24 both possess one or more antigenic determinants that are also present in the CopB protein of strain 035E.

EXAMPLE IX

Pulmonary Clearance of *M. catarrhalis* Following Passive Immunization with Monoclonal Antibodies Specific for the 30, 80, AND 100 kD OMPs The present example illustrates steps employed by the inventors in demonstrating the ability of monoclonal antibodies directed against the 30 kD, 80 kD (CopB) and HMWP OMPs to enhance pulmonary clearance of *M. catarrhalis* using a murine model system. Thus, this example demonstrates that antibodies to the 30 kD, 80 kD (CopB) or HMWP OMP may be useful for passive immunization and provides the first indication that vaccines comprising these OMPs are likely to provide active immunity against *M. catarrhalis* infections.

A. Antibody Administration

Eighteen hours prior to bacterial challenge, groups of 5 mice were passively immunized by intravenous administration of monoclonal antibody 17C7, 8B6 or 10F3. Control animals were immunized with an irrelevant antibody, 2H11, which was directed against an outer membrane protein of *Haemophilus ducreyi*. Each animal received an equivalent amount of purified antibody corresponding to 150 µg of total protein.

B. Method of Bacterial Inoculation

Mice were anaesthetized by intramuscular injection of 2 mg of ketamine HCL (Fort Dodge Lab, Fort Dodge, Iowa.) and 0.2 mg of acepromazine maleate (Fort Dodge Lab). After tracheal exposure each animal was intubated transorally with a 20 gauge intravenous catheter which was advanced until it could be visualized through the translucent tracheal wall. A PE-10 polyethylene tube containing 5 µl of bacterial suspension was then passed through the catheter into the lung where the bacteria were deposited with 150 µl of air. This technique delivered the inoculum to a localized, peripheral segment of the lung. In all the following studies, mice were challenged with *M. catarrhalis* strain 035E.

C. Pulmonary Clearance

In each study, 5 mice were sacrificed by intraperitoneal injection of 0.75 mg of sodium pentobarbital (Abbott Labs, Chicago, Ill.) immediately after inoculation (0 h), to determine bacterial deposition in the lungs. At 6 hours after challenge, experimental (17C7-, 8B6- or 10F3-immunized) and control (2H11 immunized) groups were sacrificed, and the number of viable bacteria remaining in the lungs was determined as follows: the lungs from each animal were removed aseptically and homogenized in 2 ml of sterile BHI broth in a tissue homogenizer followed by grinding in a tissue grinder until smooth. The homogenate was serially diluted in BHI broth, plated on BHI agar and incubated at 37° C. in an air incubator with a 5% $CO_2$ atmosphere for 24 h. Clearance of *M. catarrhalis* from the lungs is expressed as the percentage of colony forming units (cfu) remaining in the lung at each time point compared with the mean cfu of bacteria present at 0 hour in the same study.

Results

The mean number of viable bacteria remaining in the lungs of immunized and control mice after bolus deposition of $0.98 \times 10^5$ to $2.0 \times 10^5$ cfu of *M. catarrhalis* 035E was determined and expressed as a percentage of the initial inoculum.

TABLE IV

| Immunization Regimen | % of Bacteria Remaining at 6 h Post-Challenge | |
|---|---|---|
| | Expt. #1 | #2 |
| No immunization | 134 | 109 |
| 2H11 immunization | 113 | 108 |
| 17C7 immunization | 27 | 22 |
| 10F3 immunization | 10 | 13 |

It will be noted that Table IV does not include pulmonary clearance data for Mab 8B6. This Mab initially appeared positive, and a further study failed to duplicate this earlier positive finding as to pulmonary clearance. However, in follow-up studies it appears as though Mab 8B6 has a limited protective effect, but is not as protective as 17C7 or 10F3. In these follow-up studies (two experiments), 8B6 exhibited an average of 38% bacteria remaining at 6 hours versus about 97% for the control Mab, 2H11.

This persistence of strain 035E in the lungs of these control mice is very similar to the behavior of this strain in the lungs of normal, unimmunized, mice (Unhanand et al., 1992). In contrast, in animals passively immunized with Mab 10F3, pulmonary clearance of *M. catarrhalis* was enhanced such that the number of viable *M. catarrhalis* recovered from the lungs at 6 hours post-challenge was nearly an order of magnitude smaller than the number of organisms present in the lungs immediately after challenge.

EXAMPLE X

Pulmonary Clearance of Heterologous *M. catarrhlis* Strain Following Passive Immunization with Monoclonal Anitboidy 17C7

The present example extends the results reported above and demonstrates the ability of the monoclonal antibody 17C7, raised against the HMWP OMP from *M. catarrhalis* strain 035E, to enhance pulmonary clearance of the heterologous strain TTA24.

As described above, the monoclonal antibody 17C7 was raised against the HMWP antigen from the *M. catarrhalis* strain 035E. Results from in vitro analyses indicated that this antibody bound to all strains of *M. catarrhalis* tested, suggesting that its target antigen was present in most, if not all, strains of this organism. Administration of this antibody was found to enhance pulmonary clearance of the homologous *M. catarrhalis* strain 035E in the murine model described above.

On passively immunizing mice with the monoclonal antibody 17C7 and then challenging with the heterologous *M. catarrhalis* strain TTA24, enhanced pulmonary clearance of the TTA24 organisms was found (Table V). The positive effect of this antibody indicates that its ability to enhance pulmonary clearance is not strain-specific. This finding has important implications for the development of vaccines employing conserved *M. catarrhalis* antigens, such as those described herein, where immunization would very likely result in the generation of antibodies with the ability to enhance clearance of a wide variety of *M. catarrhalis* strains.

TABLE V

TTA24 CHALLENGE OF 17C7 IMMUNIZED MICE

| | % Bacteria remaining at 6h post-deposition | |
|---|---|---|
| Depositions | Control (2H11 Immunized) | Immune 17c7 Immunized |
| Expt. #1 $1.88 \pm 0.82 \times 10^5$ | 73.9% | 32.5% |
| Expt. #2 $2.14 \pm 1.36 \times 10^5$ | 95% | 13.5% |

EXAMPLE XI

Pulmonary Clearance of *M. catarrhalis* Following Active and Passive Immunization with *M. catarrhalis* Outer Membrane Vesicles The present example illustrates steps employed by the inventors in demonstrating that animals actively and passively immunized with outer membrane vesicles of *M. catarrhalis* also exhibit enhanced pulmonary clearance. The fact that passive immunization with antisera against OMP and LOS antigens results in enhanced pulmonary clearance of homologous and heterologous strains of *M. catarrhalis* indicates that serum antibody is involved in the clearance process and that conserved surface antigens exist in different *M. catarrhalis* strains. The success of active immunization with OMP-containing vesicles in inducing antibodies that are active against diverse *M. catarrhalis* strains in vivo further demonstrates the great potential of outer membrane vesicles (OMV) as components of *M. catarrhalis* vaccines.

A. Bacterial Strains and Culture Conditions

Two strains of *M. catarrhalis* were used in this study. Strain 035E was recovered from middle ear fluid obtained from a patient with otitis media treated at Children's Medical Center, Dallas, Tex. Strain TTA24 was isolated from a transtracheal aspirate obtained from a. patient with *M. catarrhalis* pneumonia and was obtained from Dr. Steven Berk, East Tennessee State University, Johnson City, Tenn. Both strains have previously been shown to survive and grow in the lungs of mice during the 6 hour experimental period involved in this pulmonary clearance model (Unhanand et al., 1992). These strains were grown in Brain Heart Infusion (BHI) medium (Difco Laboratories, Detroit, Mich.) at 37° C. in broth or on BHI agar plates in a 5% $CO_2$ atmosphere.

B. Preparation and Analysis of Outer Membranes and Other Bacterial Antigens

Outer membrane vesicles were prepared from BHI broth-grown whole cells of *M. catarhalis* strains 035E and TTA24 by means of the EDTA-based extraction method (Murphy, 1989). For analysis of *M. catarrhalis* LOS in the Western blot system, proteinase K-treated whole cell lysates of these two strains were prepared as described (Kimura & Hansen, 1986).

The proteins present in outer membrane vesicles were solubilized in SDS-digestion buffer, resolved by SDS-PAGE, and transferred to nitrocellulose for Western blot analysis as described (Kimura & Hansen, 1986). LOS present in proteinase K-treated whole cell lysates was resolved by SDS-PAGE and transferred to nitrocellulose for Western blot analysis (Kimura & Hansen, 1986).

C. Immunization Regimens

Both mice and rabbits were immunized with outer membrane vesicles of M. catarrhalis strain 035E prepared from broth-grown whole cells of this organism by the EDTA-based extraction method (Murphy, 1989). For the active immunization studies, female BALB/c mice (10-weeks old) received a primary immunization consisting of an intraperitoneal injection containing 50 μg of outer membrane vesicles mixed in 0.1 ml of 50% (vol/vol) Freund's Complete Adjuvant (Difco Laboratories). Four and six weeks after this primary immunization, the animals received intraperitoneal injections containing the same quantity of outer membrane vesicles suspended in 50% (vol/vol) incomplete Freund's adjuvant (Difco Laboratories). Control animals received an identical series of injections in which pH 7.2 phosphate-buffered saline (PBS) was substituted for the outer membrane vesicles. Immunized and control mice were used in pulmonary clearance studies approximately three weeks after the second booster immunization. Blood was drawn for serum preparation at this time.

To obtain large quantities of immune serum for use in passive immunization studies, adult female NZW rabbits were immunized with outer membrane vesicles from M. catarrhalis strain 035E. Each rabbit was injected at four different sites subcutaneously with a total of 100 μg of outer membrane vesicles suspended in Freund's complete adjuvant (50% vol/vol). Six weeks later, each animal received a single booster immunization consisting of a total of 50 μg of outer membrane vesicles in incomplete Freund's adjuvant, divided among four different sites. Three weeks later, blood was drawn for serum preparation. These immune sera were pooled and stored at −70° C. Passive immunization was accomplished by intraperitoneal injection of a 0.3 ml portion of the immune rabbit serum or control rabbit serum into mice 18 hours prior to bacterial challenge.

D. Pulmonary Clearance

The murine pulmonary clearance model described in section C of the previous example was employed to measure the effect of immunization on pulmonary clearance of M. catarrhalis. Immunized and control mice were anesthetized and, after exposure of the trachea, intubated transorally with a blunted 20-gauge needle which was advanced until it could be visualized through the tracheal wall. A length of very thin polyethylene tubing containing 5 μl of a suspension of M. catarrhalis cells, harvested in the logarithmic phase of growth, was passed through the needle and into the lung where the inoculum ($10^5$ colony forming units [cfu]) was expressed using 150 μl of air.

Four to five animals from both the immunized and control groups were euthanized immediately after inoculation to determine bacterial deposition in the lungs. The lungs were removed aseptically, homogenized, and the homogenates were serially diluted in BHI broth and spread onto BHI agar plates. At 6 hours post-challenge, the remaining animals (4 or 5) in both groups were euthanized and the number of viable M. catarrhalis in their lungs determined by thin same method. Clearance of M. catarrhalis from the lungs was expressed as the percentage of mean cfu remaining in the lungs after 6 hours compared with the mean cfu present at 0 time. Each study was repeated once.

Results

A. Active Immunization Against Homologous Strain

Figure 13:
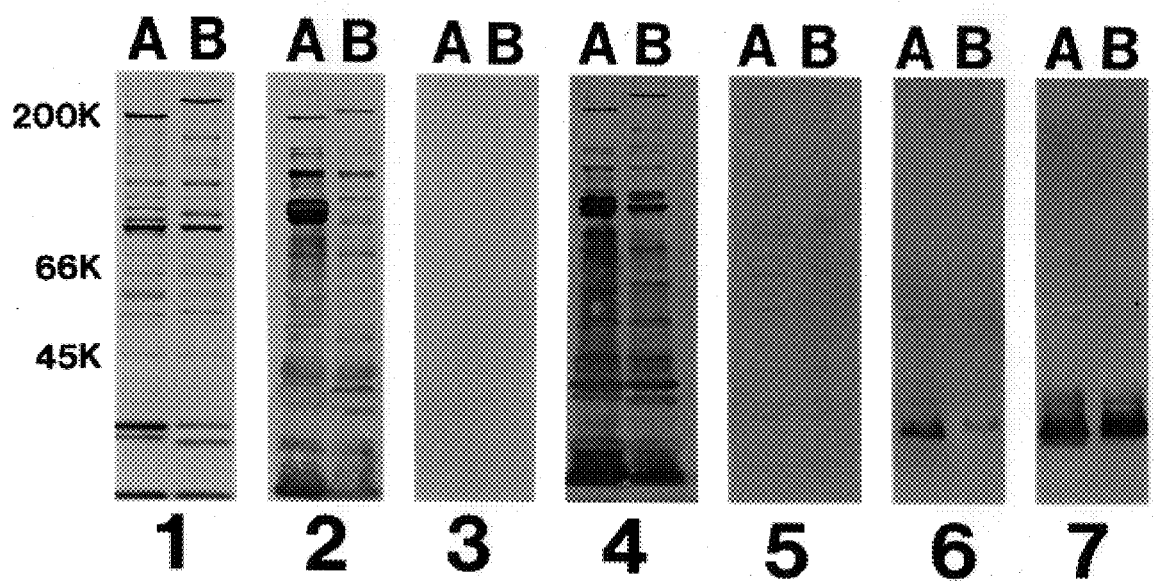
FIG. 13. Outer membrane protein profiles and immune response to outer membrane antigens of *M. catarrhalis* strains 035E (lane A) and TTA24 (lane B) as measured by Western blot analysis. Outer membrane vesicles from these strains were solubilized in SDS-digeszion buffer and the proteins were resolved by SDS-PAGE and stained with Coomassie blue (panel 1) or transferred to nitrocellulose and probed with the following primary antibodies in Western blot analysis: panel 2, immune mouse serum raised against outer membrane vesicles of strain 035E; panel 3, control serum from sham-immunized mice; panel 4, immune rabbit serum raised against outer membrane vesicles of strain 035E; panel 5, control rabbit serum. LOS present in proteinase K-treated whole cell lysates of these two *M. catarrhalis* strains was resolved by SDS-polyacrylamide gradient gel electrophoresis, transferred to nitrocellulose, and probed in Western blot analysis with either immune mouse serum (panel 6) or immune rabbit serum (panel 7) to outer membrane vesicles of strain 035E. The molecular weight position markers present on the left side of this figure pertain only to panels 1–5.

Active immunization of mice with M. catarrhalis strain 035E outer membrane vesicles resulted in the production of serum antibodies to numerous different outer membrane antigens of this bacterium, including both proteins (FIG. 13, panel 2, lane A) and LOS (FIG. 13, panel 6, lane A). contr from sham-immunized control mice was devoid of antibodies to M. catarrhalis outer membrane antigens detectable by Western blot analysis (FIG. 13, panel 3, lane A).

Active immunization enhanced the rate of clearance of M. catarrhalis strain 035E from the lungs of these animals following bolus challenge with this organism. The number of bacteria present in the lungs of the immunized animals at 6 hours post-challenge was only 13% of those present at the time of deposition (Table VI). In contrast, there was a net increase in the number of viable M. catarrhalis in the lungs of the control animals over the same time period, with the number of organisms present at 6 hours after challenge being 127% of the size of the original deposition (Table VI). This survival and modest level of growth of M. catarrhalis strain 035E in the lungs of the control mice is nearly identical to the behavior of this strain in previous studies involving unimmunized (i.e., control) mice (Unhanand et al., 1992).

TABLE VI

EFFECT OF IMMUNIZATION ON PULMONARY CLEARANCE OF MORAXELLA CATARRHALIS

| Immuniza-tion Regimen | M. catarrhalis Strain | Deposition* $10^5$ CFU (Mean ± SEM) | % Bacteria Remaining at 6 h (Mean ± SEM)* | |
|---|---|---|---|---|
| | | | Control | Immune |
| Active † | 035E | 1.45 ± 0.69 | 127 ± 55 | 13 ± 5 |
| Passive‡ | 035E | 1.88 ± 0.91 | 149 ± 43 | 48 ± 30 |
| | TTA24 | 1.72 ± 0.79 | 96 ± 22 | 35 ± 25 |

* Each value represents a mean of 8–10 animals from two independent studies.
†Animals were actively immunized by intraperitoneal injection with strain 035E outer membrane vesicles.
‡Animals were passively immunized by intraperitoneal injection with control rabbit serum or immune rabbit serum raised against strain 035E outer membrane vesicles.

B. Passive Immunization Against Homologous Strain

The results obtained with the active immunization studies, together with the observed serum antibody response to outer membrane antigens of M. catarrhalis, raised the possibility that the enhanced ability of the immunized mice to clear M. catarrhalis from their lungs involved the humoral immune response. To address this question directly, immune serum to M. catarrhalis strain 035E outer membrane vesicles was raised in rabbits for use in passive immunization studies involving the mouse model. This immune rabbit serum was shown by Western blot analysis to contain antibodies to both outer membrane proteins (FIG. 13, panel 4, lane A) and LOS (FIG. 13, panel 7, lane A) of M. catarrhalis strain 035E. Serum from control rabbits had barely detectable levels of antibody to M. catarrhalis strain 035E outer membrane antigens in Western blot analysis (FIG. 13, panel 5, lane A) .

Passive immunization of mice with this immune rabbit serum resulted in the enhanced clearance of M. catarrhalis strain 035E from the lungs of these animals. Only 48% of the number of bacteria originally deposited in the lungs of the immunized animals remained at 6 hours, whereas the number of M. catarrhalis in the lungs of the control animals increased to 149% of the original deposition (Table VI).

C. Passive Immunization Against Heterologous Strain

A second, heterologous strain of *M. catarrhalis* was also used in these challenge studies involving mice passively immunized with the immune rabbit serum to outer membrane vesicles of strain 035E. *M. catarrhalis* strain TTA24 (FIG. 13, panel 1, lane B) has an outer membrane protein profile in SDS-PAGE that is different from that of strain 035E (FIG. 13, panel 1, lane A). The immune rabbit serum raised against strain 035E outer membrane vesicles exhibited readily detectable reactivity with the outer membrane proteins of strain TTA24 (FIG. 13, panel 4, lane B). This same immune rabbit. serum contained antibodies that bound the LOS of strain TTA24 (FIG. 13, panel 7, lane B). It should also be noted that the immure mouse serum (from the mice actively immunized with outer membrane vesicles of strain 035E) contained antibodies that cross-reacted extensively with the outer membrane antigens of strain TTA24 (FIG. 13, panel 2, lane B, and panel 6, lane B).

Mice passively immunized with this immune rabbit serum raised against strain 035E also were able to clear the heterologous *M. catarrhalis* strain from their lungs more rapidly than animals immunized with control serum. The enhancement of pulmonary clearance of the heterologous strain by passive immunization was very similar to that observed with the homologous strain, in that the number of *M. catarrhalis* strain TTA24 cfu remaining in the lungs of the immunized animals at the 6 hour time point was 35% of the original deposition (Table VI). While this heterologous strain did not grow quite as readily in the lungs of control mice as did the homologous strain (Table VI), it is interesting to note that the number of cfu of each strain present in the lungs of the immunized animals at the 6 hour time point was ⅓ of those present in the lungs of the control animals (Table VI).

The fact that active immunization with *M. catarrhalis* outer membrane vesicles resulted in enhanced clearance of this organism from the lungs after bolus challenge (Table VI) indicates that immune factors can affect the interaction of this bacterium with the lower respiratory tract. Moreover, the positive effect of passive immunization with immune serum on pulmonary clearance (Table VI) indicates that serum antibodies likely play a major role in the observed inmunoprotection. The protection observed against pulmonary challenge with a heterologous *M. catarrhalis* strain is particularly encouraging. These results indicate that one or more surface antigens of this organism are conserved between these distinct strains and that they are targets for antibodies which function to enhance clearance of these organisms from the lungs. Taken together, the results of this study strongly suggest that this murine model system has potential for use in the continuing development of vaccine candidates, particularly using the *M. catarrhalis* outer membrane antigens of the present invention.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting in kind or amount of the biological action. All such modifications are intended to be included within the scope of the appended claims.

REFERENCES

The following references, to the extent that they provide exemplary procedural or other details supplementary to those set forth herein, are specifically incorporated herein by reference.

Adelman et al. (1983) *DnA* 2: 183
Berk (1990) *Arch. Intern. Med.* 150: 2254–2257
Bolivar et al. (1977) *Gene* 2: 95
Catlin (1990) *Clin. Microbiol. Rev.* 3: 293–320
Chang et al. (1978) *Nature* 375: 615
Chapman et al. (1985) *J. Infect. Dis.* 151: 878–882
Consensus (1989), *Pediater. Infect. Dis. J.*, 8: S94–S97
Crea et al. (1978), *Proc. Natl. Acad. Sci. U.S.A* 75: 5765
Devereux et al. (1984) *Nucl. Acids Res.* 12: 387–395
Doern (1986) *Diag. Microbiol. Infect. Dis.* 4: 191–201
Doyle (1989) *Peditr. Infect. Dis. J.* 8(suppl): S45–7
Eichenlaub, R. (1979) *J. Bacteriol* 138: 559–566
EPO Appl. Publ. No. 0036776
Ey et al.. (1978), *Immunochem* 5: 429–436
Faden et al. (1990) *Pediatr. Infect. Dis. J.* 9: 623–626
Faden et al. (1991) *Ann. Otol. Rhinol. Laryngol.* 100: 612–615
Faden et al. (1992) *Infect. Immun.* 60: 3824–3829
Fiers et al. (1978) *Nature* 273: 113
Goeddel et al. (1979) *Nature* 281: 544
Goeddel et al. (1980) *Aucleic Acids Res.* 8: 4057
Goldblatt et al. (1990), *Jrnl. Infect. Dis.*, 162: 1128–1135
Guan et al. (1987) *Gene*, 67: 21–30
Gulig et al. (1987) *Infect. Immun.* 55: 513–520
Hanson & Hansen (1991) *Molec. Microbiol.* 5: 267–278
Hess et al. (1968) *J. Adv. Enzyme Reg.* 7: 149
Hitzeman et al. (1980) *J. Biol. Chem.* 255: 2073
Holland et al. (1978) *Biochemistry* 17: 4900
Hunkapiller et al. (1983) Meth. Enzymol. 91: 227–236
Itakura et al. (1977) *Science* 198: 1056
Jones (1977) *Genetics* 85: 12
Kimura et al. (1985) *Infect. Immun.* 47: 253–259
Kimura & Hansen (1986) *Infect. Immun.* 50: 69–79
Kingsman et al. (1979) *Gene* 7: 141
Kyte & Doolittle (1982) *J. Mol. Biol.* 157: 105–132
Leinonen et al. (1981) J. Infect. Dis. 144: 570–574
Marchant (1990) *Am. J. Med.* 88(Suppl. 5A): 15S–19S
Matsudaira (1987) *J. Biol. Chem.* 262: 10035–10038
McGehee (1989) *Am. J. Respir. Cell Mol. Biol.* 1: 201–210
Melendez & Johnson (1990) *Rev. Infect. Dis.* 13: 428–429
Messing et al. (1981) Third Cleveland Symposium on Macromolecules and Recombinant DNA, Editor A. Walton, Elsevier, Amsterdam
Murphy (1989), *Pediat. Infect. Dis. J.*, 8: S75–S77
Murphy & Loeb (1989). *Microb. Pathog.* 6: 159–174
Murphy et al. (1990), *Am. Jrnl. Med.*, 88: 5A-41S–5A-45S
Nagai and Thogersen (1987) *Meth. Enzymol.*, 153: 461–487
Nikaido & Vaara (1985). *Microbiol. Rev.* 49: 1–32
Patrick et al. (1987), *Infect. Immun.*, 55: 2902–2911
Sambrook et al. (1989). Molecular cloning: A laboratory manual.
Cold Spring Harbor Laboratory. Cold Spring Harbor, N.Y.
Sanger et al. (1977) *Proc. Natl. Acad. Sci. USA* 74: 5463–5467
Sarubbi et al. (1990) *An. J. Med.* 88(Suppl. 5A): 9S–14S
Schonheyder & Ejlertsen (1989). *Eur. J. Clin. Microbiol. Infect.*
Dis. 8: 299-300
Stinchcomb et al. (1979) Nature 282: 39
Tabor and Richardson (1985) *Proc. Natl. Acad. Sci.*, 82: 1074–1078 *Tissue Culture*, Academic Press, Kruse and Patterson, editors (1973)
Tschemper et al. (1980) *Gene* 10: 157
Unhanand et al. (1992) *J. Infect. Dis.* 165: 644–650
Vaneechoutte (1990) *J. clin. Microbiol.* 28: 182–187

What is claimed is:

1. An antigen composition prepared according to a method comprising:

introducing a recombinant expression vector including a DNA segment coding for the 80 kD copB antigen into a recombinant host cell;

culturing the recombinant host cell under conditions effective to allow expression of the encoded 80 kD copB antigen; and collecting said expressed antigen.

2. A purified *M. catarrhalis* 80 kD CopB outer membrane protein.

3. A method for inducing an antibody response to *M. catarrhalis* 80 kD copB antigen in an animal, comprising administering to the animal an immunologically effective amount of purified *M. catarrhalis* 80 kD coPB antigen.

4. The method of claim 3, wherein the *M. catarrhalis* 80 kD CopB outer membrane protein is a recombinant protein.

5. The method of claim 3 wherein an antigen composition is administered to the animal, the composition comprising purified *M. catarrhalis* outer membrane vesicles in combination with purified *M. catarrhalis* 80 kD CopB outer membrane protein.

6. The antigen of claim 2, further defined as recombinantly produced 80 kD copB antigen.

7. An antigen composition comprising purified 80 kD copB antigen, purified essentially free from other *M. catarrhalis* outer membrane antigens.

8. The antigen composition of claim 7, consisting essentially of the *M. catarrhalis* 80 kD copB outer membrane antigen.

9. The antigen composition of claim 7, wherein the *M. catarrhalis* 80 kD copB outer membrane antigen includes an amino acid-sequence consisting of that set forth in SEQ ID NO:2.

10. The antigen composition of claim 7, wherein the *M. catarrhalis* 80 kD copB outer membrane antigen is recombinantly produced.

11. The antigen composition of claim 7, wherein the composition comprises a pharmaceutically acceptable carrier or diluent.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2520 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
TCAATAAGTT GGAGTCATTA CCTGATTTTA GTAAGTAGAT GAGCAAGGGA TAATTTGACA      60

AAAACAAATT TGATTTCAAG CCTCATAATC GGAGTTATTA TGAATAAGTT TCAATTATTA     120

CCGCTGACAT TGGCGGTGAG TGCCGCTTTT ACAACCACTG CTTTTGCAGC TGTTAGCCAG     180

CCTAAGGTTG TCTTGGCAGG CGATACAGTG GTCAGTGATC GCCAAGGTGC AAAAATTAAA     240

ACCAATGTTG TTACCTTACG AGAAAAAGAC GAAAGCACGG CTACAGATTT GCGTGGTTTG     300

TTACAAGATG AACCTGCCAT CGGTTTTGGC GGTGGTAATG GTACTTCTCA ATTTATCAGC     360

ATTCGTGGCA TGGGTCATAA TGCCATTGAC CTAAAAATTG ACAACGCTTA TCAAGATGGT     420

CAATTACACT ACCACCAAGG TCGCTTTATG CTAGACCCCC AGATGGTCAA AGTCGTTTCG     480

GTACAAAAAG GGGCAGGCTT TGCCAGTGCA GGCATTGGGG CAACCAATGG TGCGATTGTT     540

ACCAAAACCT TAGATGCTGA TGAGCTTTTA AGAAACAGCG ACAAAGATTA TGGCTTTAAA     600

GTTGGTGCAG GCTTATCAAC CAACAAAGGT CATTCTTATC ATGGTAGTGC CTTTGGTAAA     660

GCACAGACAG GAGGCAATGA TGTGGTTACA AGAAGTGCCT TGGATAAATC CAGTTACCTT     720

GTCAAGGCAG GGCTAACTGC TGGCGATCAT CGATTTTTTG GTCAGGTAGA TGCCCTTGTC     780

TCTTATAATC AAGTAAATGA CAGCGACTAT AAAGGCGGTA AAGGGTACAC CAATCTGTTG     840

GTGGTCAGCC ATCTAAATGA AGTTCATAAA GGCATTCGTG GCGTGCGTGA AGAGTTTGAC     900

TTCGCCAATC GTGCCTTGAC GCTAGATATA GAAAAAGATA AGAAAAAACG TACTGACGAA     960

CAGCTTCAGG CAGAGTTAGA TAACAAATAT GCAGGCAAGG GTTACAAACT TGGCAGTAAA    1020

ACACCAGATG GTAAAAAGTA TAATGTGGTT GATGCCAATG GTAAATTGGT GGCTGATTTA    1080

GATAGGAACA ACCCAACTCA GCGTGAAACC TACCAAAAGT TAACCAACCT TGAATGGACA    1140

GGTAAAAACC TTGGTTTTGC AAATGAAGTT ACTGCCAATG TCTATAAGTT AGAACATGGA    1200

CGCAACTCCT CTAGCGATAA AGGTAACAGC TATATTCTTC GTGATGTACC TAATACCATC    1260

AATGATAACG GTGATAGCCC ATCAAATATG CATGTGGTAG CCACAGGGGC TAATATTAAT    1320

TTTGATAAAG AATTTAATCA CGGTCTATTA AAAGGCTTTG GCGTTGACCA TACTTTATTA    1380

AAATATGGCA TCAACTATCG CCATCAAGAA GCTGTACCGC CTAGAGGTAT TAGACCTGGT    1440

TTTCAAAACC AAGAAAAAAC CGATGCTGGC ATTTATCTAG AAGCGGTTAA CCAAATCAAT    1500

GACTTTACCA TCAATACAGG CGTGCGTGTT GACCGTTTTG ACTTTAAAGC TATGGACGGT    1560

AAAAAGGTTG GAAAAACCGA CATCAACCCA AGCTTTGGGG TGATTTATGA TGTCAATCCT    1620

AATCTTAGCG TCAGCGGTAA CCTAATCTAT GCCACTCGCA GCCCACGCTT TGCTGATGCT    1680

ATCCTAAGCC GTGGCTTCCG TGATGGCGTT GTGAGTATTG CTGATAACGC AAAAGCAGAA    1740
```

```
AAAGCACGCA ATACCGAGAT TGGTTTTAAC TATAATAATG GGCCATATAC CGCCTTTGGC    1800

AGCTATTTTT GGCAGCGTGT GGATAATGCC AGAGCTACTG CCGATGCTGT ACAACACCCC    1860

ACAGTTACAA CAGCTAAGAT TACCTATCTT GGCAACCAAG GTCATCAGAC CAACCACGGT    1920

TATGAGCTGG GCGTAGGCTA TACCGAAGGT GCGTGGCGTG CGCGTGCTGG CGTTGCTCAC    1980

AGCAAGCCAA CCATGCACAA TGTCAAATTT AAAGCCAACC CTGAATATGC CGTGCGTACA    2040

GGTCGTACAT GGACAGCAGA TGTCGCCTAT CGCCTGCCAA ACCCCAGTGT AGAGCTTGGT    2100

GTGAGACACA CATTGGTTGA AGGGGTAGAT GCCAAAGACA CTTCTATCCT TAGCGGTAAA    2160

TTTGATGATA AAGATGGTGC TATTCTTAAC CGTGAAGGCT ATAATGTCAG TGACATCTAT    2220

GCCAACTGGA AGCCTTATGG CAATGATAAG GTGAATGTAA ACTTTGCGGT GAATAATGTC    2280

TTTAATAAAA ACTATCGCCC ACACACTCAG CGTGCTTCCA TAGATACCTT ACCTGGGGCA    2340

GGTCGTGATT TCCGTGTTGG CGTGAACTTC ACTTACTAAT ACTTGCCGAT TTATCGGTAT    2400

AATACTGAAC ACTCAAGCAC GCTTGGGTGT TCTTTTTATG GGTATGAGTG GATAAAAACG    2460

ATAAAAAAAG CCAATCGTAT CATATTGATT GGCTATAATG ATAAAATTAA ATCATTACTG    2520
```

(2) INFORMATION FOR SEQ ID NO:2:

(i) SEQUENCE CHARACTERISTICS:
        (A) LENGTH: 759 amino acids
        (B) TYPE: amino acid
        (C) STRANDEDNESS:
        (D) TOPOLOGY: linear (xi) SEQUENCE DESCRIPTION: SEQ ID NO:2:

```
Met Asn Lys Phe Gln Leu Leu Pro Leu Thr Leu Ala Val Ser Ala Ala
1               5                  10                  15

Phe Thr Thr Thr Ala Phe Ala Ala Val Ser Gln Pro Lys Val Val Leu
            20                  25                  30

Ala Gly Asp Thr Val Val Ser Asp Arg Gln Gly Ala Lys Ile Lys Thr
        35                  40                  45

Asn Val Val Thr Leu Arg Glu Lys Asp Glu Ser Thr Ala Thr Asp Leu
    50                  55                  60

Arg Gly Leu Leu Gln Asp Glu Pro Ala Ile Gly Phe Gly Gly Asn
65                  70                  75                  80

Gly Thr Ser Gln Phe Ile Ser Ile Arg Gly Met Gly His Asn Ala Ile
                85                  90                  95

Asp Leu Lys Ile Asp Asn Ala Tyr Gln Asp Gly Gln Leu His Tyr His
                100                 105                 110

Gln Gly Arg Phe Met Leu Asp Pro Gln Met Val Lys Val Ser Val
            115                 120                 125

Gln Lys Gly Ala Gly Phe Ala Ser Ala Gly Ile Gly Ala Thr Asn Gly
        130                 135                 140

Ala Ile Val Thr Lys Thr Leu Asp Ala Asp Glu Leu Leu Arg Asn Ser
145                 150                 155                 160

Asp Lys Asp Tyr Gly Phe Lys Val Gly Ala Gly Leu Ser Thr Asn Lys
                165                 170                 175

Gly His Ser Tyr His Gly Ser Ala Phe Gly Lys Ala Gln Thr Gly Phe
                180                 185                 190

Gly Gln Val Asp Ala Leu Val Ser Tyr Asn Gln Val Asn Asp Ser Asp
            195                 200                 205

Tyr Lys Gly Gly Lys Gly Tyr Thr Asn Leu Leu Gly Asn Asp Val Val
        210                 215                 220
```

-continued

```
Thr Arg Ser Ala Leu Asp Lys Ser Ser Tyr Leu Val Lys Ala Gly Leu
225                 230                 235                 240

Thr Ala Gly Asp His Arg Phe Val Val Ser His Leu Asn Glu Val His
            245                 250                 255

Lys Gly Ile Arg Gly Val Arg Glu Glu Phe Asp Phe Ala Asn Arg Ala
        260                 265                 270

Leu Thr Leu Asp Ile Glu Lys Asp Lys Lys Arg Thr Asp Glu Gln
    275                 280                 285

Leu Gln Ala Glu Leu Asp Asn Lys Tyr Ala Gly Lys Gly Tyr Lys Leu
290                 295                 300

Gly Ser Lys Thr Pro Asp Gly Lys Lys Tyr Asn Val Val Asp Ala Asn
305                 310                 315                 320

Gly Lys Leu Val Ala Asp Leu Asp Arg Asn Asn Pro Thr Gln Arg Glu
            325                 330                 335

Thr Tyr Gln Lys Leu Thr Asn Leu Glu Trp Thr Gly Lys Asn Leu Gly
        340                 345                 350

Phe Ala Asn Glu Val Thr Ala Asn Val Tyr Lys Leu Glu His Gly Arg
    355                 360                 365

Asn Ser Ser Asp Lys Gly Asn Ser Tyr Ile Leu Arg Asp Val Pro
370                 375                 380

Asn Thr Ile Asn Asp Asn Gly Asp Ser Pro Ser Asn Met His Val Val
385                 390                 395                 400

Ala Thr Gly Ala Asn Ile Asn Phe Asp Lys Glu Phe Asn His Gly Leu
            405                 410                 415

Leu Lys Gly Phe Gly Val Asp His Thr Leu Leu Lys Tyr Gly Ile Asn
        420                 425                 430

Tyr Arg His Gln Glu Ala Val Pro Pro Arg Gly Ile Arg Pro Gly Phe
    435                 440                 445

Gln Asn Gln Glu Lys Thr Asp Ala Gly Ile Tyr Leu Glu Ala Val Asn
450                 455                 460

Gln Ile Asn Asp Phe Thr Ile Asn Thr Gly Val Arg Val Asp Arg Phe
465                 470                 475                 480

Asp Phe Lys Ala Met Asp Gly Lys Lys Val Gly Lys Thr Asp Ile Asn
            485                 490                 495

Pro Ser Phe Gly Val Ile Tyr Asp Val Asn Pro Asn Leu Ser Val Ser
        500                 505                 510

Gly Asn Leu Ile Tyr Ala Thr Arg Ser Pro Arg Phe Ala Asp Ala Ile
    515                 520                 525

Leu Ser Arg Gly Phe Arg Asp Gly Val Val Ser Ile Ala Asp Asn Ala
530                 535                 540

Lys Ala Glu Lys Ala Arg Asn Thr Glu Ile Gly Phe Asn Tyr Asn Asn
545                 550                 555                 560

Gly Pro Tyr Thr Ala Phe Gly Ser Tyr Phe Trp Gln Arg Val Asp Asn
            565                 570                 575

Ala Arg Ala Thr Ala Asp Ala Val Gln His Pro Thr Val Thr Thr Ala
        580                 585                 590

Lys Ile Thr Tyr Leu Gly Asn Gln Gly His Gln Thr Asn His Gly Tyr
    595                 600                 605

Glu Leu Gly Val Gly Tyr Thr Glu Gly Ala Trp Arg Ala Arg Ala Gly
610                 615                 620

Val Ala His Ser Lys Pro Thr Met His Asn Val Lys Phe Lys Ala Asn
625                 630                 635                 640

Pro Glu Tyr Ala Val Arg Thr Gly Arg Thr Trp Thr Ala Asp Val Ala
            645                 650                 655
```

```
Tyr Arg Leu Pro Asn Pro Ser Val Glu Leu Gly Val Arg His Thr Leu
            660                 665                 670

Val Glu Gly Val Asp Ala Lys Asp Thr Ser Ile Leu Ser Gly Lys Phe
        675                 680                 685

Asp Asp Lys Asp Gly Ala Ile Leu Asn Arg Glu Gly Tyr Asn Val Ser
    690                 695                 700

Asp Ile Tyr Ala Asn Trp Lys Pro Tyr Gly Asn Asp Lys Val Asn Val
705                 710                 715                 720

Asn Phe Ala Val Asn Asn Val Phe Asn Lys Asn Tyr Arg Pro His Thr
                725                 730                 735

Gln Arg Ala Ser Ile Asp Thr Leu Pro Gly Ala Gly Arg Asp Phe Arg
            740                 745                 750

Val Gly Val Asn Phe Thr Tyr
        755

(2) INFORMATION FOR SEQ ID NO:3:

(i) SEQUENCE CHARACTERISTICS:
        (A) LENGTH: 2520 base pairs
        (B) TYPE: nucleic acid
        (C) STRANDEDNESS: single
        (D) TOPOLOGY: linear (ix) FEATURE:
         (A) NAME/KEY: CDS
         (B) LOCATION: 100..2376

(xi) SEQUENCE DESCRIPTION: SEQ ID NO:3:

TCAATAAGTT GGAGTCATTA CCTGATTTTA GTAAGTAGAT GAGCAAGGGA TAATTTGACA        60

AAAACAAATT TGATTTCAAG CCTCATAATC GGAGTTATT ATG AAT AAG TTT CAA         114
                                           Met Asn Lys Phe Gln
                                             1               5

TTA TTA CCG CTG ACA TTG GCG GTG AGT GCC GCT TTT ACA ACC ACT GCT        162
Leu Leu Pro Leu Thr Leu Ala Val Ser Ala Ala Phe Thr Thr Thr Ala
                10                  15                  20

TTT GCA GCT GTT AGC CAG CCT AAG GTT GTC TTG GCA GGC GAT ACA GTG        210
Phe Ala Ala Val Ser Gln Pro Lys Val Val Leu Ala Gly Asp Thr Val
                25                  30                  35

GTC AGT GAT CGC CAA GGT GCA AAA ATT AAA ACC AAT GTT GTT ACC TTA        258
Val Ser Asp Arg Gln Gly Ala Lys Ile Lys Thr Asn Val Val Thr Leu
        40                  45                  50

CGA GAA AAA GAC GAA AGC ACG GCT ACA GAT TTG CGT GGT TTG TTA CAA        306
Arg Glu Lys Asp Glu Ser Thr Ala Thr Asp Leu Arg Gly Leu Leu Gln
    55                  60                  65

GAT GAA CCT GCC ATC GGT TTT GGC GGT GGT AAT GGT ACT TCT CAA TTT        354
Asp Glu Pro Ala Ile Gly Phe Gly Gly Gly Asn Gly Thr Ser Gln Phe
70                  75                  80                  85

ATC AGC ATT CGT GGC ATG GGT CAT AAT GCC ATT GAC CTA AAA ATT GAC        402
Ile Ser Ile Arg Gly Met Gly His Asn Ala Ile Asp Leu Lys Ile Asp
                90                  95                 100

AAC GCT TAT CAA GAT GGT CAA TTA CAC TAC CAC CAA GGT CGC TTT ATG        450
Asn Ala Tyr Gln Asp Gly Gln Leu His Tyr His Gln Gly Arg Phe Met
            105                 110                 115

CTA GAC CCC CAG ATG GTC AAA GTC GTT TCG GTA CAA AAA GGG GCA GGC        498
Leu Asp Pro Gln Met Val Lys Val Val Ser Val Gln Lys Gly Ala Gly
        120                 125                 130

TTT GCC AGT GCA GGC ATT GGG GCA ACC AAT GGT GCG ATT GTT ACC AAA        546
Phe Ala Ser Ala Gly Ile Gly Ala Thr Asn Gly Ala Ile Val Thr Lys
    135                 140                 145

ACC TTA GAT GCT GAT GAG CTT TTA AGA AAC AGC GAC AAA GAT TAT GGC        594
```

```
             Thr Leu Asp Ala Asp Glu Leu Leu Arg Asn Ser Asp Lys Asp Tyr Gly
             150             155                 160                 165

TTT AAA GTT GGT GCA GGC TTA TCA ACC AAC AAA GGT CAT TCT TAT CAT                642
Phe Lys Val Gly Ala Gly Leu Ser Thr Asn Lys Gly His Ser Tyr His
            170                 175                 180

GGT AGT GCC TTT GGT AAA GCA CAG ACA GGA TTT GGT CAG GTA GAT GCC                690
Gly Ser Ala Phe Gly Lys Ala Gln Thr Gly Phe Gly Gln Val Asp Ala
            185                 190                 195

CTT GTC TCT TAT AAT CAA GTA AAT GAC AGC GAC TAT AAA GGC GGT AAA                738
Leu Val Ser Tyr Asn Gln Val Asn Asp Ser Asp Tyr Lys Gly Gly Lys
            200                 205                 210

GGG TAC ACC AAT CTG TTG GGC AAT GAT GTG GTT ACA AGA AGT GCC TTG                786
Gly Tyr Thr Asn Leu Leu Gly Asn Asp Val Val Thr Arg Ser Ala Leu
215                 220                 225

GAT AAA TCC AGT TAC CTT GTC AAG GCA GGG CTA ACT GCT GGC GAT CAT                834
Asp Lys Ser Ser Tyr Leu Val Lys Ala Gly Leu Thr Ala Gly Asp His
230                 235                 240                 245

CGA TTT GTG GTC AGC CAT CTA AAT GAA GTT CAT AAA GGC ATT CGT GGC                882
Arg Phe Val Val Ser His Leu Asn Glu Val His Lys Gly Ile Arg Gly
                250                 255                 260

GTG CGT GAA GAG TTT GAC TTC GCC AAT CGT GCC TTG ACG CTA GAT ATA                930
Val Arg Glu Glu Phe Asp Phe Ala Asn Arg Ala Leu Thr Leu Asp Ile
            265                 270                 275

GAA AAA GAT AAG AAA AAA CGT ACT GAC GAA CAG CTT CAG GCA GAG TTA                978
Glu Lys Asp Lys Lys Lys Arg Thr Asp Glu Gln Leu Gln Ala Glu Leu
            280                 285                 290

GAT AAC AAA TAT GCA GGC AAG GGT TAC AAA CTT GGC AGT AAA ACA CCA                1026
Asp Asn Lys Tyr Ala Gly Lys Gly Tyr Lys Leu Gly Ser Lys Thr Pro
            295                 300                 305

GAT GGT AAA AAG TAT AAT GTG GTT GAT GCC AAT GGT AAA TTG GTG GCT                1074
Asp Gly Lys Lys Tyr Asn Val Val Asp Ala Asn Gly Lys Leu Val Ala
310                 315                 320                 325

GAT TTA GAT AGG AAC AAC CCA ACT CAG CGT GAA ACC TAC CAA AAG TTA                1122
Asp Leu Asp Arg Asn Asn Pro Thr Gln Arg Glu Thr Tyr Gln Lys Leu
                330                 335                 340

ACC AAC CTT GAA TGG ACA GGT AAA AAC CTT GGT TTT GCA AAT GAA GTT                1170
Thr Asn Leu Glu Trp Thr Gly Lys Asn Leu Gly Phe Ala Asn Glu Val
            345                 350                 355

ACT GCC AAT GTC TAT AAG TTA GAA CAT GGA CGC AAC TCC TCT AGC GAT                1218
Thr Ala Asn Val Tyr Lys Leu Glu His Gly Arg Asn Ser Ser Ser Asp
            360                 365                 370

AAA GGT AAC AGC TAT ATT CTT CGT GAT GTA CCT AAT ACC ATC AAT GAT                1266
Lys Gly Asn Ser Tyr Ile Leu Arg Asp Val Pro Asn Thr Ile Asn Asp
            375                 380                 385

AAC GGT GAT AGC CCA TCA AAT ATG CAT GTG GTA GCC ACA GGG GCT AAT                1314
Asn Gly Asp Ser Pro Ser Asn Met His Val Val Ala Thr Gly Ala Asn
390                 395                 400                 405

ATT AAT TTT GAT AAA GAA TTT AAT CAC GGT CTA TTA AAA GGC TTT GGC                1362
Ile Asn Phe Asp Lys Glu Phe Asn His Gly Leu Leu Lys Gly Phe Gly
                410                 415                 420

GTT GAC CAT ACT TTA TTA AAA TAT GGC ATC AAC TAT CGC CAT CAA GAA                1410
Val Asp His Thr Leu Leu Lys Tyr Gly Ile Asn Tyr Arg His Gln Glu
            425                 430                 435

GCT GTA CCG CCT AGA GGT ATT AGA CCT GGT TTT CAA AAC CAA GAA AAA                1458
Ala Val Pro Pro Arg Gly Ile Arg Pro Gly Phe Gln Asn Gln Glu Lys
            440                 445                 450

ACC GAT GCT GGC ATT TAT CTA GAA GCG GTT AAC CAA ATC AAT GAC TTT                1506
Thr Asp Ala Gly Ile Tyr Leu Glu Ala Val Asn Gln Ile Asn Asp Phe
            455                 460                 465

ACC ATC AAT ACA GGC GTG CGT GTT GAC CGT TTT GAC TTT AAA GCT ATG                1554
```

```
Thr Ile Asn Thr Gly Val Arg Val Asp Arg Phe Asp Phe Lys Ala Met
470                 475                 480                 485

GAC GGT AAA AAG GTT GGA AAA ACC GAC ATC AAC CCA AGC TTT GGG GTG        1602
Asp Gly Lys Lys Val Gly Lys Thr Asp Ile Asn Pro Ser Phe Gly Val
                490                 495                 500

ATT TAT GAT GTC AAT CCT AAT CTT AGC GTC AGC GGT AAC CTA ATC TAT        1650
Ile Tyr Asp Val Asn Pro Asn Leu Ser Val Ser Gly Asn Leu Ile Tyr
            505                 510                 515

GCC ACT CGC AGC CCA CGC TTT GCT GAT GCT ATC CTA AGC CGT GGC TTC        1698
Ala Thr Arg Ser Pro Arg Phe Ala Asp Ala Ile Leu Ser Arg Gly Phe
        520                 525                 530

CGT GAT GGC GTT GTG AGT ATT GCT GAT AAC GCA AAA GCA GAA AAA GCA        1746
Arg Asp Gly Val Val Ser Ile Ala Asp Asn Ala Lys Ala Glu Lys Ala
    535                 540                 545

CGC AAT ACC GAG ATT GGT TTT AAC TAT AAT AAT GGG CCA TAT ACC GCC        1794
Arg Asn Thr Glu Ile Gly Phe Asn Tyr Asn Asn Gly Pro Tyr Thr Ala
550                 555                 560                 565

TTT GGC AGC TAT TTT TGG CAG CGT GTG GAT AAT GCC AGA GCT ACT GCC        1842
Phe Gly Ser Tyr Phe Trp Gln Arg Val Asp Asn Ala Arg Ala Thr Ala
                570                 575                 580

GAT GCT GTA CAA CAC CCC ACA GTT ACA ACA GCT AAG ATT ACC TAT CTT        1890
Asp Ala Val Gln His Pro Thr Val Thr Thr Ala Lys Ile Thr Tyr Leu
            585                 590                 595

GGC AAC CAA GGT CAT CAG ACC AAC CAC GGT TAT GAG CTG GGC GTA GGC        1938
Gly Asn Gln Gly His Gln Thr Asn His Gly Tyr Glu Leu Gly Val Gly
        600                 605                 610

TAT ACC GAA GGT GCG TGG CGT GCG CGT GCT GGC GTT GCT CAC AGC AAG        1986
Tyr Thr Glu Gly Ala Trp Arg Ala Arg Ala Gly Val Ala His Ser Lys
    615                 620                 625

CCA ACC ATG CAC AAT GTC AAA TTT AAA GCC AAC CCT GAA TAT GCC GTG        2034
Pro Thr Met His Asn Val Lys Phe Lys Ala Asn Pro Glu Tyr Ala Val
630                 635                 640                 645

CGT ACA GGT CGT ACA TGG ACA GCA GAT GTC GCC TAT CGC CTG CCA AAC        2082
Arg Thr Gly Arg Thr Trp Thr Ala Asp Val Ala Tyr Arg Leu Pro Asn
                650                 655                 660

CCC AGT GTA GAG CTT GGT GTG AGA CAC ACA TTG GTT GAA GGG GTA GAT        2130
Pro Ser Val Glu Leu Gly Val Arg His Thr Leu Val Glu Gly Val Asp
            665                 670                 675

GCC AAA GAC ACT TCT ATC CTT AGC GGT AAA TTT GAT GAT AAA GAT GGT        2178
Ala Lys Asp Thr Ser Ile Leu Ser Gly Lys Phe Asp Asp Lys Asp Gly
        680                 685                 690

GCT ATT CTT AAC CGT GAA GGC TAT AAT GTC AGT GAC ATC TAT GCC AAC        2226
Ala Ile Leu Asn Arg Glu Gly Tyr Asn Val Ser Asp Ile Tyr Ala Asn
    695                 700                 705

TGG AAG CCT TAT GGC AAT GAT AAG GTG AAT GTA AAC TTT GCG GTG AAT        2274
Trp Lys Pro Tyr Gly Asn Asp Lys Val Asn Val Asn Phe Ala Val Asn
710                 715                 720                 725

AAT GTC TTT AAT AAA AAC TAT CGC CCA CAC ACT CAG CGT GCT TCC ATA        2322
Asn Val Phe Asn Lys Asn Tyr Arg Pro His Thr Gln Arg Ala Ser Ile
                730                 735                 740

GAT ACC TTA CCT GGG GCA GGT CGT GAT TTC CGT GTT GGC GTG AAC TTC        2370
Asp Thr Leu Pro Gly Ala Gly Arg Asp Phe Arg Val Gly Val Asn Phe
            745                 750                 755

ACT TAC       TAATACTTGC CGATTTATCG GTATAATACT GAACACTCAA GCACGCTTGG   2426
Thr Tyr

GTGTTCTTTT TATGGGTATG AGTGGATAAA AACGATAAAA AAAGCCAATC GTATCATATT      2486

GATTGGCTAT AATGATAAAA TTAAATCATT ACTG                                  2520
```

(2) INFORMATION FOR SEQ ID NO:4:

(i) SEQUENCE CHARACTERISTICS:
   (A) LENGTH: 759 amino acids
   (B) TYPE: amino acid
   (D) TOPOLOGY: linear (ii) MOLECULE TYPE: protein (xi) SEQUENCE DESCRIPTION: SEQ ID NO:4:

```
Met Asn Lys Phe Gln Leu Leu Pro Leu Thr Leu Ala Val Ser Ala Ala
 1               5                  10                  15

Phe Thr Thr Thr Ala Phe Ala Ala Val Ser Gln Pro Lys Val Val Leu
            20                  25                  30

Ala Gly Asp Thr Val Val Ser Asp Arg Gln Gly Ala Lys Ile Lys Thr
        35                  40                  45

Asn Val Val Thr Leu Arg Glu Lys Asp Glu Ser Thr Ala Thr Asp Leu
    50                  55                  60

Arg Gly Leu Leu Gln Asp Glu Pro Ala Ile Gly Phe Gly Gly Asn
65                  70                  75                  80

Gly Thr Ser Gln Phe Ile Ser Ile Arg Gly Met Gly His Asn Ala Ile
                85                  90                  95

Asp Leu Lys Ile Asp Asn Ala Tyr Gln Asp Gly Gln Leu His Tyr His
            100                 105                 110

Gln Gly Arg Phe Met Leu Asp Pro Gln Met Val Lys Val Val Ser Val
            115                 120                 125

Gln Lys Gly Ala Gly Phe Ala Ser Ala Gly Ile Gly Ala Thr Asn Gly
    130                 135                 140

Ala Ile Val Thr Lys Thr Leu Asp Ala Asp Glu Leu Leu Arg Asn Ser
145                 150                 155                 160

Asp Lys Asp Tyr Gly Phe Lys Val Gly Ala Gly Leu Ser Thr Asn Lys
                165                 170                 175

Gly His Ser Tyr His Gly Ser Ala Phe Gly Lys Ala Gln Thr Gly Phe
            180                 185                 190

Gly Gln Val Asp Ala Leu Val Ser Tyr Asn Gln Val Asn Asp Ser Asp
        195                 200                 205

Tyr Lys Gly Gly Lys Gly Tyr Thr Asn Leu Leu Gly Asn Asp Val Val
    210                 215                 220

Thr Arg Ser Ala Leu Asp Lys Ser Ser Tyr Leu Val Lys Ala Gly Leu
225                 230                 235                 240

Thr Ala Gly Asp His Arg Phe Val Val Ser His Leu Asn Glu Val His
                245                 250                 255

Lys Gly Ile Arg Gly Val Arg Glu Glu Phe Asp Phe Ala Asn Arg Ala
            260                 265                 270

Leu Thr Leu Asp Ile Glu Lys Asp Lys Lys Arg Thr Asp Glu Gln
        275                 280                 285

Leu Gln Ala Glu Leu Asp Asn Lys Tyr Ala Gly Lys Gly Tyr Lys Leu
    290                 295                 300

Gly Ser Lys Thr Pro Asp Gly Lys Lys Tyr Asn Val Val Asp Ala Asn
305                 310                 315                 320

Gly Lys Leu Val Ala Asp Leu Asp Arg Asn Asn Pro Thr Gln Arg Glu
                325                 330                 335

Thr Tyr Gln Lys Leu Thr Asn Leu Glu Trp Thr Gly Lys Asn Leu Gly
            340                 345                 350

Phe Ala Asn Glu Val Thr Ala Asn Val Tyr Lys Leu Glu His Gly Arg
        355                 360                 365

Asn Ser Ser Ser Asp Lys Gly Asn Ser Tyr Ile Leu Arg Asp Val Pro
```

-continued

```
            370                 375                 380
Asn Thr Ile Asn Asp Asn Gly Asp Ser Pro Ser Asn Met His Val Val
385                 390                 395                 400

Ala Thr Gly Ala Asn Ile Asn Phe Asp Lys Glu Phe Asn His Gly Leu
                405                 410                 415

Leu Lys Gly Phe Gly Val Asp His Thr Leu Leu Lys Tyr Gly Ile Asn
                420                 425                 430

Tyr Arg His Gln Glu Ala Val Pro Pro Arg Gly Ile Arg Pro Gly Phe
        435                 440                 445

Gln Asn Gln Glu Lys Thr Asp Ala Gly Ile Tyr Leu Glu Ala Val Asn
    450                 455                 460

Gln Ile Asn Asp Phe Thr Ile Asn Thr Gly Val Arg Val Asp Arg Phe
465                 470                 475                 480

Asp Phe Lys Ala Met Asp Gly Lys Lys Val Gly Lys Thr Asp Ile Asn
                485                 490                 495

Pro Ser Phe Gly Val Ile Tyr Asp Val Asn Pro Asn Leu Ser Val Ser
                500                 505                 510

Gly Asn Leu Ile Tyr Ala Thr Arg Ser Pro Arg Phe Ala Asp Ala Ile
                515                 520                 525

Leu Ser Arg Gly Phe Arg Asp Gly Val Val Ser Ile Ala Asp Asn Ala
                530                 535                 540

Lys Ala Glu Lys Ala Arg Asn Thr Glu Ile Gly Phe Asn Tyr Asn Asn
545                 550                 555                 560

Gly Pro Tyr Thr Ala Phe Gly Ser Tyr Phe Trp Gln Arg Val Asp Asn
                565                 570                 575

Ala Arg Ala Thr Ala Asp Ala Val Gln His Pro Thr Val Thr Thr Ala
                580                 585                 590

Lys Ile Thr Tyr Leu Gly Asn Gln Gly His Gln Thr Asn His Gly Tyr
                595                 600                 605

Glu Leu Gly Val Gly Tyr Thr Glu Gly Ala Trp Arg Ala Arg Ala Gly
        610                 615                 620

Val Ala His Ser Lys Pro Thr Met His Asn Val Lys Phe Lys Ala Asn
625                 630                 635                 640

Pro Glu Tyr Ala Val Arg Thr Gly Arg Thr Trp Thr Ala Asp Val Ala
                645                 650                 655

Tyr Arg Leu Pro Asn Pro Ser Val Glu Leu Gly Val Arg His Thr Leu
                660                 665                 670

Val Glu Gly Val Asp Ala Lys Asp Thr Ser Ile Leu Ser Gly Lys Phe
                675                 680                 685

Asp Asp Lys Asp Gly Ala Ile Leu Asn Arg Glu Gly Tyr Asn Val Ser
        690                 695                 700

Asp Ile Tyr Ala Asn Trp Lys Pro Tyr Gly Asn Asp Lys Val Asn Val
705                 710                 715                 720

Asn Phe Ala Val Asn Asn Val Phe Asn Lys Asn Tyr Arg Pro His Thr
                725                 730                 735

Gln Arg Ala Ser Ile Asp Thr Leu Pro Gly Ala Gly Arg Asp Phe Arg
                740                 745                 750

Val Gly Val Asn Phe Thr Tyr
                755
```